United States Patent [19]  [11]  4,043,979
Cram  [45]  Aug. 23, 1977

[54] POLYMER-MULTIHETEROMACROCYCLES

[75] Inventor: Donald J. Cram, Los Angeles, Calif.

[73] Assignee: The Regents of the University of California, Berkeley, Calif.

[21] Appl. No.: 672,211

[22] Filed: Mar. 31, 1976

Related U.S. Application Data

[60] Division of Ser. No. 448,333, March 5, 1974, Pat. No. 4,001,279, which is a continuation-in-part of Ser. No. 346,089, March 29, 1973, abandoned.

[51] Int. Cl.$^2$ ............................................. C08F 12/08
[52] U.S. Cl. ................................................. 260/47 UP
[58] Field of Search ................................... 260/47 UP

[56] References Cited

U.S. PATENT DOCUMENTS

| 3,225,118 | 12/1965 | De Melio | 260/47 UP |
| 3,336,259 | 8/1967 | Zimmerman et al. | 260/47 UP |
| 3,682,872 | 8/1972 | Brizzolara et al. | 260/47 UP X |

Primary Examiner—Ethel G. Love
Attorney, Agent, or Firm—John T. Reynolds

[57] ABSTRACT

Chiral, hinged, asymmetric host binaphthyl-based multiheteromacrocycles of oxygen covalently bonded to styrene/divinylbenzene copolymers are provided. These new compounds have specific chiral recognition properties, which properties make these new compounds useful for separating or resolving racemic and other mixtures of amino acids, amino acid esters and salts thereof for either or both of analytical purposes or large scale manufacturing procedures.

6 Claims, No Drawings

POLYMER-MULTIHETEROMACROCYCLES

Work on this invention was supported in part by the U.S. Public Health Service Research Grant No. GM 12640-12 from the Department of Health, Education and Welfare and by a grant from the National Science Foundation, GP 33533X.

CROSS REFERENCES

This application is a division of application Ser. No. 448,333, filed Mar. 5, 1974 now U.S. Pat. No. 4,001,279, which is a continuation-in-part of application Ser. No. 346,089, filed Mar. 29, 1973 now abandoned.

INTRODUCTION

This invention relates to chiral, hinged, asymmetric host multiheteromacrocycles of the oxygen type which are useful to afford selective complexation of specific guest substances. More particularly, this invention provides such compounds covalently bound to a styrene/-divinylbenzene copolymer.

BACKGROUND OF THE INVENTION

Macrocylces, and particularly macrocyclic polyethers, are known compounds and have been referred to in the literature as "crown" compounds in reference to the crownlike appearance of the polyalkoxy cyclic chain in the molecular structural model. Such compounds are disclosed in U.S. Pat. Nos. 3,562,295, 3,686,225, and 3,687,978.

These prior art "crown" compounds are characterized as composed of alkyleneoxy chains, particularly ethyleneoxy chains, or ethyleneoxy chains upon which is fused a phenylene or cyclohexylene radical in one or more positions, examples being 2,3,11,12-dibenzo-1,4,7,10,13,16-hexoxacyclooctadeca-2,11-diene and 2,5,8,15,18,21-hexoxatricyclo-[20.4.0$^{9.14}$] hexacosane disclosed in the U.S. Pat. No. 3,687,978. These prior compounds are known to form complexeswith a wide variety of ionic metal compounds, and they have been suggested as useful agents in carrying normally insoluble reaget substances into solution in nonhydroxylic media.

Such crown compounds have been described extensively in the literature, for example:
J. Am. Spc. 89 2495-6
J.Am. Chem. Soc. 89 7017-36
J. Am. Chem. Soc. 92 386-91
J. Am. Chem. Soc. 92 391-94
J. Org. Chem. 36 254-57
Angew. Chem. Int. Ed. 11 16-25
Fed. Proc. 27 1305-08
Endeavor 30 142-6
J.Am. Chem. soc. 92 4321-30
J. Am. Chem. Soc. 93 2231-35
J. Am. Chem. Soc. 93 2235-43

In the article, Angew. Chem. Int. Ed. 11 16-25, there is disclosed a system of nomenclature whereby such crown compounds can be referred to with greater simplicity of language than is required by the formal systems of nomenclature for organic compounds.

Although the compounds of this invention contain ethyleneoxy units, they do not possess the necessary overall structural features of "crowns". Crown compounds possess high symmetry elements, and none of their atoms are rigidly held far from the best plane of the oxygen atoms. The macrocycles described here are all asymmetric, and contain rigid planes of atoms held perpendicular to the best plane of the macrocycle, and which extend above and below that plane. Crown compounds contain patterns of

units, and in some cases

units. The macrocycles described here contain at least one

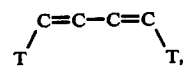

each pair of carbon atoms being incorporated in a different aromtic ring. In these formulas T stands for O. although some of the macrocycles described here possess some of the properties of crown compounds, many of the properties of the presently described macrocycles are unique, and are not shared by crown compounds.

Prior macrocycles noted above also include those which contain sulfur in the cycle in place of oxygen, and a number have been described in J. Org. Chem. 36 254-57 wherein sulfur atoms replace one to four oxygen atoms in crown-5, crown-6, and crown-7 compounds.

In the prior compounds, macrocycles containing up to 4 fused rings have been described, each ring being either a benzene or a cyclohexyl ring.

In the latter patent specifically referred to above, such macrocycles containing additional nuclear substituents on the aromatic rings are described.

The prior macrocycles are all characterized by high molecular symmetry, and have an ability to complex other substances such as metal cations, depending upon the size of the hole of the crown and the diameter of the cation. All rings fused to the crowns are situated on the periphery of the macrocycle by involvements of 1,2-linkages, or at most, 1,3-linkages. Such fused rings involve a pair of vicinal carbon atoms including broadly such rings as phenylene, naphthylene, phenylanthrylene, anthrylene, cyclohexylene, and the like.

The prior art compounds, particularly those involving peripherally fused rings, are prepared by utilizing a vicinal dihydric phenol such as catechol which is caused to react with a dihalide containing ether oxygen atoms. By selecting the appropriate dihalide and adjusting reaction conditions, the macrocycles can be formed relatively simply. More complex crowns can be formed using the vicinal dihydric phenol in which on hydroxyl group has been blocked to achieve partial reaction with the dihalide, followed by unblocking and further reaction with dihalide.

SUMMARY OF THE INVENTION

Briefly, this invention provides some new chiral, hinged, asymmetric host multiheteromacrocycles of oxygen-containing binaphthyl linkages in the macrocycle ring system covalently bound to a solid form styrene/divinylbenzene copolymer via an ether linkage. The host ring system can be unsubstituted or substituted with methyl groups in the naphthyl ring positions ortho to the macrocycle oxygen linkage. The host macrocycle ring can be in the RR or SS configuration. The useful solid support for the macrocycles is styrene copolymerized and cross-linked with divinylbenzene, and is known as polymer. It has been found according to this invention that these styrene/-divinylbenzene copolymers are particularly well suited for use as a substrate matrix to support the host ring systems of this invention. These new polymer host compounds are useful in analytical and commercial scale chromatography columns for analyzing or separating into optically pure isomers complex mixtures of racemic and other mixtures of guest substances, e.g., amino acids, or the amino acid ester and ester salt forms of such amino acids by virtue of their specific chiral recognition properties.

This invention also provides some new hydroxyethyl-host intermediate compounds which are useful as starting materials for preparing the above new polymer/-host multiheteromacrocycles of this invention.

DETAILED DESCRIPTION OF THE INVENTION

More specifically, this invention provides some new compounds of the formula

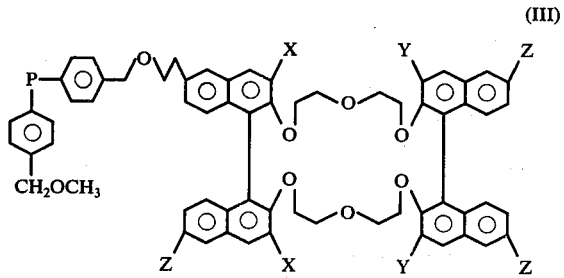

(III)

where P is the backbone of a solid styrene/divinylbenzene copolymer, each Z is H or $CH_2CH_2OH$, each X is either H or $CH_3$, each Y is either H or $CH_3$, and the binaphthyl groups of the macrocycle are in the (RR)— or (SS)-configuration. Preferred compounds are those wherein the oxygen-containing macrocycle has X as $CH_3$, and Y is methyl or hydrogen and Z is H.

The new hydroxyethylated host compounds of this invention which are used to prepare the above polymer/host compounds are those of the formula

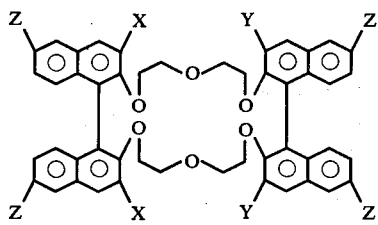

wherein at least one Z is —$CH_2CH_2OH$ and the remaining Z moieties are hydrogen or —$CH_2CH_2OH$, each X is hydrogen or methyl, each Y is hydrogen or methyl and the binaphthyl groups of the mecrocycle are in the (SS) or (RR) configuration. An example of a preferred compound of this type is one wherein one Z is —$CH_2CH_2OH$, the remaining Z moieties are hydrogen, each X is methyl and each Y is hydrogen.

The styrene/divinylbenzene copolymers useful for making the compounds of this invention are known compounds and generally comprise a p-substituted polystyrene cross-linked with from about 1 to 25 percent of divinylbenzene. Those copolymers that are of low divinylbenzene content swell in organic solvents and shrink in aqueous solvents. They are rigid enough for use as packing substrate in chromatography or separation columns for liquid passage through the copolymer-host matrix. Preferred styrene/divinylbenzene copolymers are toward the upper range of divinylbenzene content, do not swell, are solid materials, contain about 300 to 400 square meters per gram, and have between 10 and 20 percent of their benzene rings present at their surfaces, and which when chloromethylated by known procedures will give between 1 and 2 milliequivalents of chlorine per gram of material. Examples of styrene/-divinylbenzene polymers useful in making the compounds of this invention are those referred to in the *Journal of Chromatographic Science*, Vol. 12, September 1974, pages 507–411. A particularly useful, commercially available form of styrene/divinylbenzene copolymer for this purpose is a highly cross-linked polystrene/divinylbenzene macroreticular resin having surface phenyl rings which can be chloromethylated or otherwise functionalized to react with a reactive form of a host macrocycle compound. An example includes a styrene/divinylbenzene copolymer, known under the trade name Amberlite XAD-2, which has a surface area of about 330 square meters per gram, and which has about 14 percent of its benzene rings present at the interface. Chloromethylation of all of these rings will give about 1.12 milliequivalents of chlorine per gram of material. Method of chloromethylating benzene rings of polymer systems are now known. For example, a R. H. Grubbs et al. Communication to the Editor in the Journal of the American Chemical Society, Vol. 95, pp. 2373–75 (1973) discloses a procedure for chloromethylating a divinylbenzene/styrene copolymer is preparation for its use in other reactions.

The multiheteromacrocyclic host compounds which are prepared to covalently bond to the chloromethylated sytrene-divinylbenzene copolymer to give the polymer/host compounds of this invention can be functionalized to contain up to 4 possible points of attachment. However, it is statistically probable that only one possible point of attachment is used by the multiheteromacrocycles even when in principle more are available. Two points of attachment would result in large ring formation that involves the rigid host and the rigid polymer as parts of the same ring. The chances of the proper spacing being available for more than a very few molecules are very low.

In preparation for reaction with the chloromethylated styrene-divinylbenzene copolymer, the host molecules are first functionalized to effect formation of hydroxyethyl groups on at least one naphthyl ring carbon atom of the host compound. This can be done by a sequence of chemical operations which can be summrized as halogenation, preferably bromination, lithiation followed by ethoxylation with ethylene oxide. Adventitious moisture present in the lithiation and ethoxylation always gives product in which some or all bromines have been replaced with hydrogen. Detailed examples illustrating this procedure for making the compounds of this invention follow.

Measured amounts of the hydroxyethylated host compound (usually in excess) and the chloromethylated styrenedivinylbenzene copolymer can be reacted in dry tetrahydrofuran in the presence of sodium hydride and under nitrogen, followed by heating at reflux until the reaction has gone as far as possible. Analysis of the polymer produced for chlorine coupled with the amount of recovered non-attached host from the reaction mixture provides measures of how much host has become covalently attached to the polymer. The polymer is then heated with methanol-sodium methoxide to replace as many as possible of the unreacted chloromethyl groups of the polymer with methoxymethyl groups.

The systematic names of most of the host compounds described are too complicated for ready translation into structural formulas. Therefore structural formulas will be assigned unique numbers, and the specific compounds will be coupled to their structures by these numbers. The numbers assigned structures are the same in parent case U.S. application Ser. No. 346,089, filed Mar. 29, 1973 and U.S. application Ser. No. 448,333, filed Mar. 5, 1974, which are incorporated herein by reference thereto. All of the multiheteromacrocycles (referred to frequently as macrocycles) contain 1,1'binaphthyl units which are non-superimposable on their mirror images, and are therefore "handed", or chiral. Even through chiral or asymmetric, many of the compounds contain symmetry elements, such as $C_2$ axes. A $C_2$ is an axis passed through a molecular structure such that rotation of the structure about that axis by 180° reproduces the exact structure. A consequence of a chiral macrocycle possessing a $C_2$ axis is that the same structure is produced when a second chiral species complexes either the top or bottom face of the macrocycle. Such a cycle in effect lacks sidedness. The term "face"refers to the best plane of the macrocycle's oxygens. The hole of the macrocycle is the space enclosed by the oxygens of the macrocycle when those oxygens are turned inward, and are close to being coplanar. The terms "monolocular", and "dilocular" refer to how the space above (or below) the face of a multiheteromacrocycle is divided. When the space is broken on one face by only one naphthalene ring that protrudes above or below the face of the macrocycle, the system is monolocular. When the space is divided into two parts, the system is dilocular. The compounds described here (lll) are dilocular, and the space is divided both above and below the two faces by 1,1'-dinaphthyl units, whose naphthalene rings are perpendicular to the faces, and which act as walls, or barriers. Since the 1,1'-binaphthyl units are chiral, the barriers are chiral barriers. The spaces between naphthalene rings of different units are referred to as cavities. Cavities can be chiral if their dimensions are defined by chiral barriers. The term "host molecule" refers to a macrocycle capable of complexing a guest molecule or ion. The term "chiral recognition" refers to the ability of a chiral host of a given configuration to recognize through differential complexation the configuration of a chiral guest entity. Chiral recognition arises from a complementary vs a non-complementary steric fit of host to guest in a complex. The relationships between hands and gloves provide an analogy. Right hands fit right gloves only, and left hands fit left gloves only. The symbols L, M and S attached to an asymmetric center of a potential guest molecule refer to the relative size of the three substituents as large, medium and small, respectively. The symbols L', M', and S' refer to the relative sizes of cavities of the host molecules.

Each cycle's oxygens provide neutral ligands for alkylammonium cations. When complexed, the oxygens of the host turn inward, and are roughly coplanar. The macrocyclic ring is attached at the two 2-positions of each binaphthyl unit. The two 3-positions of each binaphthyl unit direct the attached side chains X or Y alongside the hole, and further defined the shapes of the cavities. The 6-positions of the naphthalene rings are remote from hole and cavity, and the presence or absence of groups in these positions play only minor roles in determining the binding character of the host. Groups attached at the 6-positions are used to covalently bind the host to the resin, that acts as a solid support for the host.

The above uniquely cooperating molecular properties of the polymer/host compounds (lll) lead to their use as agents for optical resolution by differential complexation between (RR)-lll or (SS)-lll and the enantionmers of such substances as α- and β-amino acids of racemic and other mixtures of primary amine, amino acid, aminoester or amino amide salts (guest substances). Complexes between polymer/-host (RR)-lll as host and a guest of the (R) configuration have a different stability from and are diastereomerically related to complexes between polymer-host (RR)-lll as host and the same guest of the (S) configuration. The question of which diastereomeric complex is the more stable frequently can be predicted in advance of experiment on steric groups by examination of Corety-Pauling-Koltun molecular models of the two complexes. This invention makes use of diastereomeric differential complexation at the phase interface between the polymer containing the chiral macrocycle, and the two enantiomeric amine salts contained in a solvent or gas phase in contact with the polymer/host compound.

The absolute configurations of the optically active host compounds are known. Because of the complementary stereochemical structures of host and guest in the more stable diastereomeric complex the absolute configurations of the more complexed guest entities can be inferred. By use of the multiplate complexation-decomplexation processes of chromatography both optical enantiomers of guests can be produced from their racemates, and criteria for optical purity developed. The general formulas of the two diastereomerically related complexes are formulated.

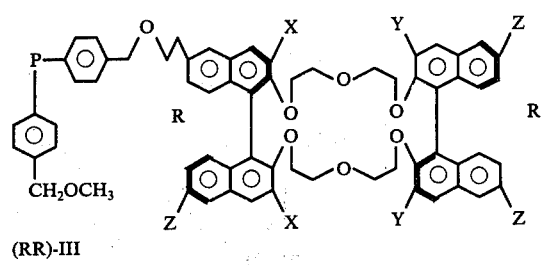

(RR)-III

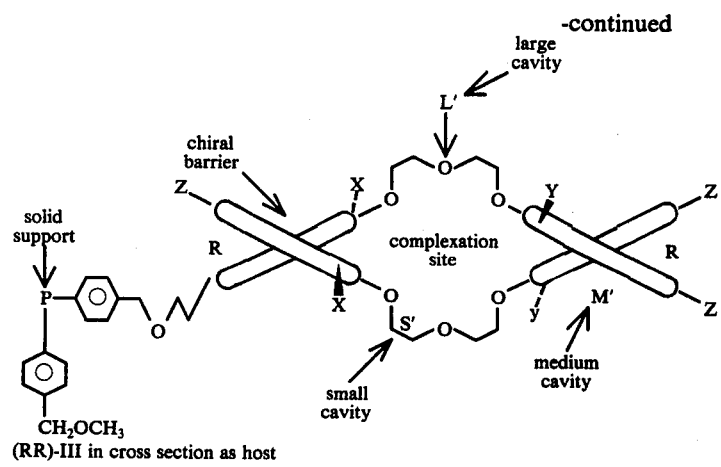
(RR)-III in cross section as host
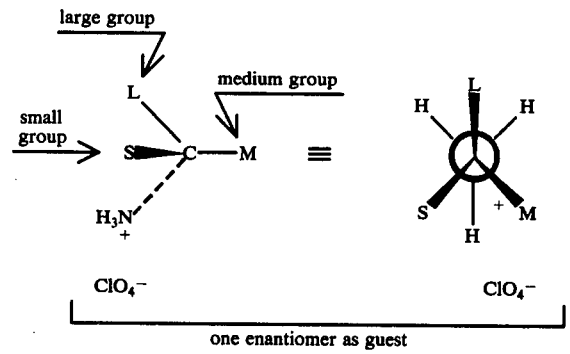
one enantiomer as guest
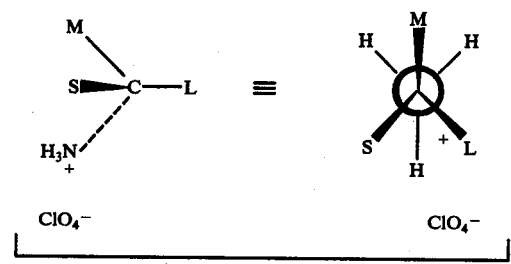
other enantiomer as guest
equal parts of each enantiomer mixed is racemate
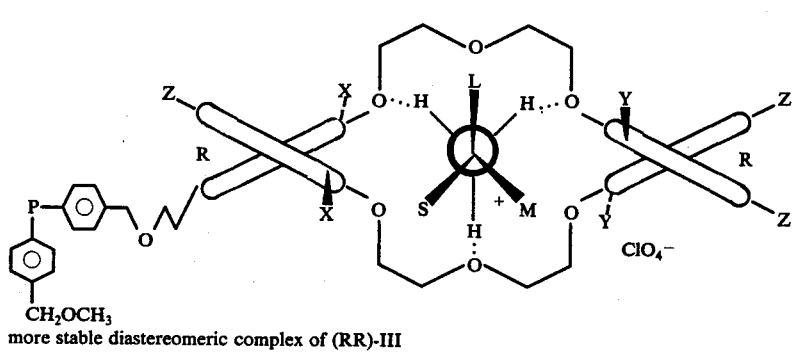
more stable diastereomeric complex of (RR)-III
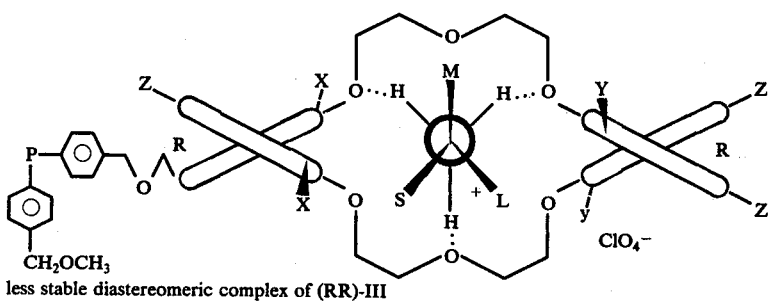
less stable diastereomeric complex of (RR)-III Description of Syntheses of the Polyheteromacrocycles 448,333, supra, but is reviewed in the following reaction sequence.

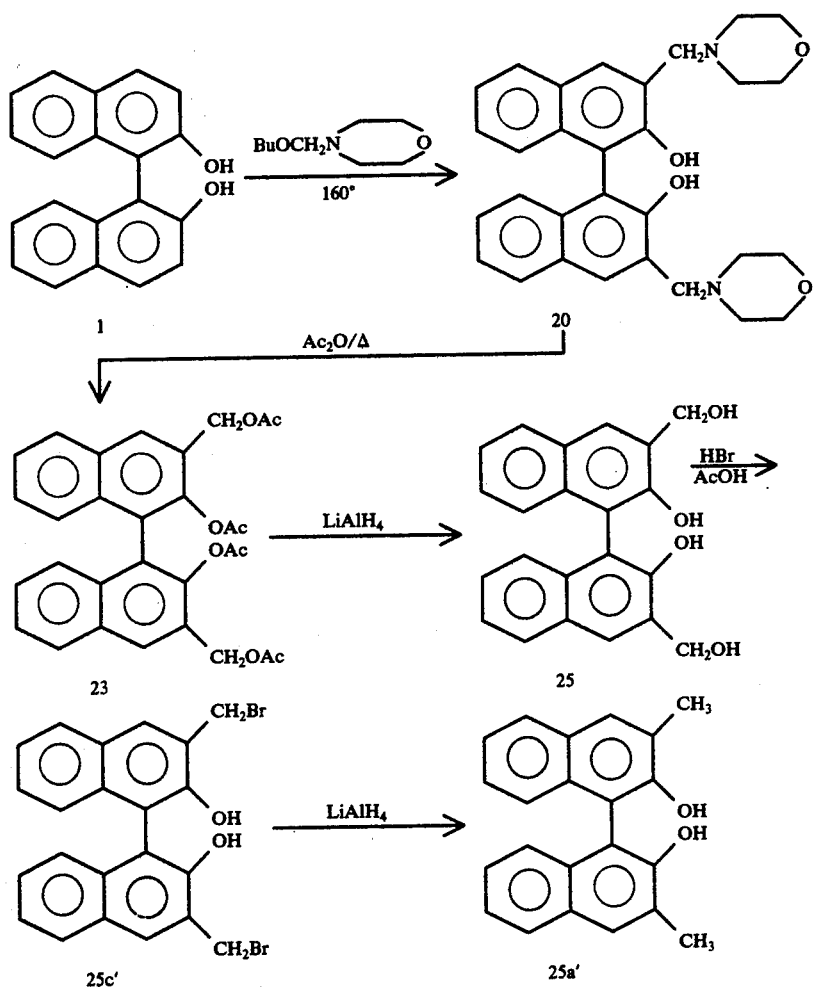

wherein the symbols Bu denotes butyl and Ac denotes acetyl.

Racemic 25a′ was resolved to give its two optically pure enantiomers, (−)-(S)-25a′ and (−)-(R)-25a′, which are formulated both in the ordinary and cross-sectional way. The absolute configurations of the enantiomers were determined by circular dichroism (CD) curve comparisons of the enantiomers of 1 and of 25 [Tetrahedron, 27, 5999 (1971)] and those of 25a′.

The primary starting materials for all systems were 2,2′-dihydroxy 1,1′-binaphthyl (1) in a racemic or opticlaly pure state, (−)-(S)-1 or (+)-(R)-1. The absolute configurations and rotations of the enantiomers of 1 have been established[Tetrahedron, 27, 5999 (1971)] and are formulated both in a conventional and in a cross-sectional way which will be useful. The symbols (S) and (R) name the configuration, and the symbols (−) and (+) the signs of rotation.

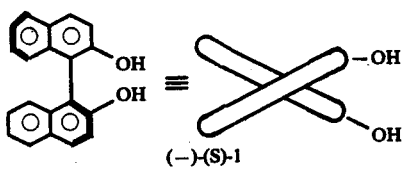

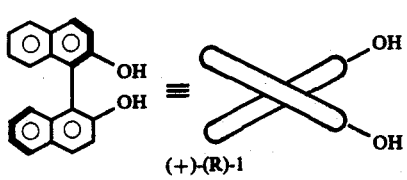

A secondary starting material is racemic 25a′, whose preparation was described in parent case Ser. No.

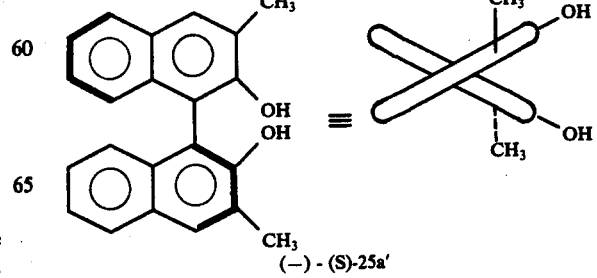

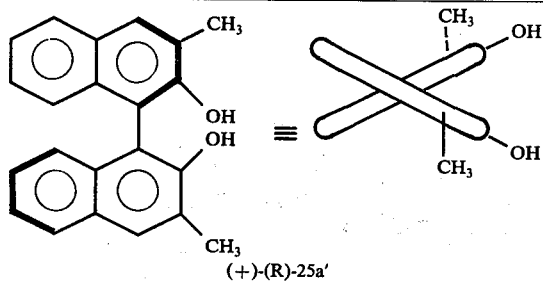

(+)-(R)-25a'

Bromination of (+)-(R)-1 gave (−)-(R)-127, and bromination of (+)-(R)-25a' gave (−)-(R)-128. Similarly, (−)-(S)-25a' gave (+)-(S)-128. Similarly, (−)-(S)-1 gives (+)-(S)-127.

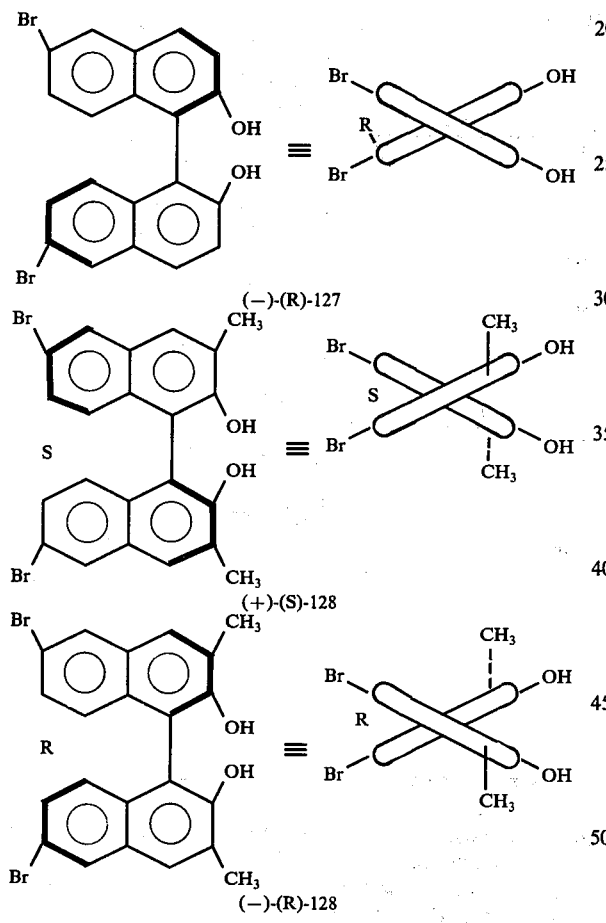

Optically pure forms of 1, 25a', 127 and 128 proved stable to conditions required to convert them to multiheteromacrocycles (alkali metal bases such as sodium hydride, potassium hydroxide, sodium hydroxide or potassium or sodium alkoxides in solvents sch as tetrahydrofuran or dimethylformamide).

A mixture of 1 with two moles of sodium hydroxide and the monopyranyl ether of diethyleneglycol monochloride gave a bis-pyranyl ether, cleavage of which with acid gave diol. Treatment of diol with p-toluenesulfonyl chloride (tosylation) gave 1a. Here and elsewhere, the symbol Ts stands for the tosyl or p-toluenesulfonlyl group. Similarly (−)-(S)-1a and (+)-(R)-1a were prepared. Similarly, from 25a' and its enantiomers were prepared 25d', (+)-(S)-25d' and (−)-(R)-25d', respectively.

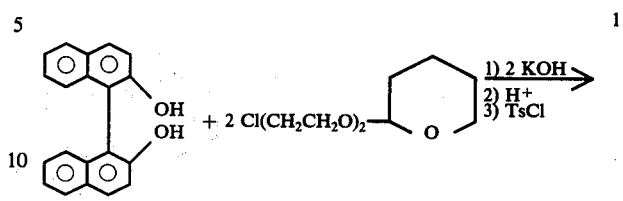

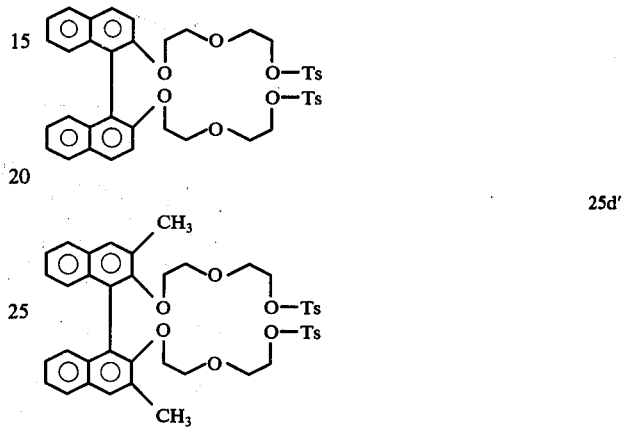

The two enantiomers of the simplest dilocular system, (−)-(SS)-8 and (+)-(RR)-8, were prepared by treating (−)-(S)-1 and (+)-(R)-1 (respectively) with diethylene glycol ditosylate and potassium tert-butoxide in tetrahydrofuran. In Ser. No. 448,333 (page 95) was reported this synthesis of (−)-(SS)-8. Also reported (Ser. No. 448,333, pages 95–97) was the synthesis of racemic and (SR)-8, and (+)-(RR)-8, (Ser. No. 448,333, page 180). In a new method that leads to a single cyclic product, diol (−)-(S)-1 and ditosylate (−)-(S)-1a with potassium hydroxide gave (−)-(SS)-8. Similarly, (+)-(R)-1 and (+)-(R)-1a gave (+)-(RR)-8. The optical rotations of the two enantiomers of 8 made by these diverse methods are in substantial agreement with each other, a fact that indicates they are opticaly pure.

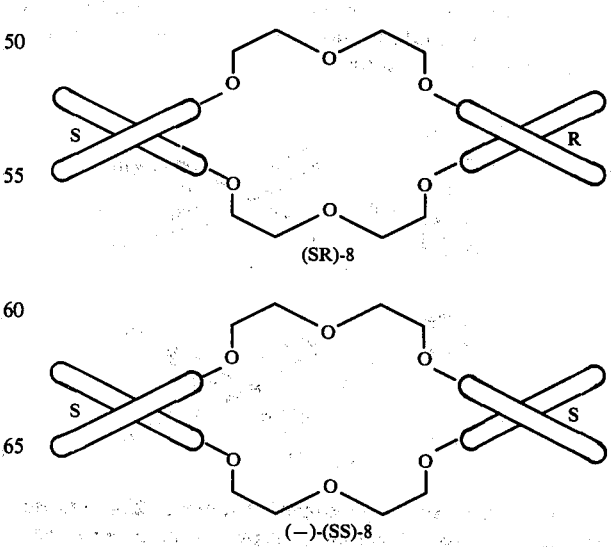

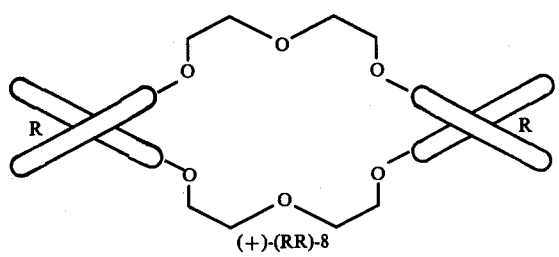

(+)-(RR)-8

In Ser. No. 448,333, supra, (pages 160 and 164a), the host syntheses and characterizations of racemic 48c', (−)-(SR)-48c'), (−)-(SS)-48c' and (+)-(RR)-48c' were described, and their absolute configurations were established by their methods of syntheses. Here simpler syntheses of (−)-(SS)-48c' and (+)-(RR)-48c' are reported. Treatment of dimethyldiol (+)-(R)-25a' with ditosylate (+)-(R)-1a and base gave dimethyl cycle (+)-(RR)-48c'. Likewise diol (+)-(R)-1 and dimethyl ditosylate (−)-(R)-25d'gave (+)-(RR)-48c'. Similarly diol (−)-(S)-1 and ditosylate (+)-(S)-25d' gave (−)-(SS)-48c'. The optical rotations of the two enantiomers of 48c' made by these diverse methods are in substantial agreement with each other, a fact that indicates they are optically pure.

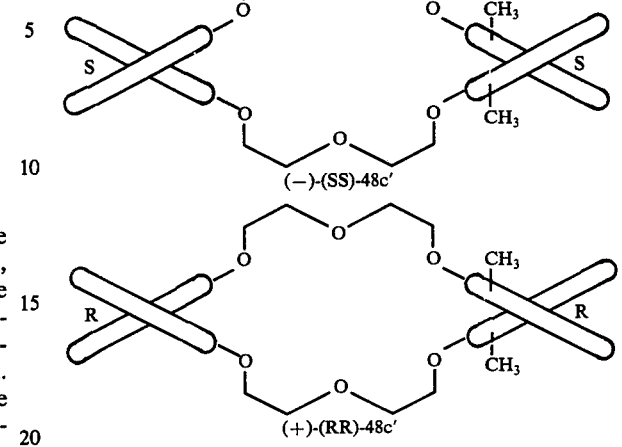

(−)-(SS)-48c'

(+)-(RR)-48c'

In application Ser. No. 448,333 (pages 158–159), racemic and meso -48b' (tetramethylcycles) were described. Here we report the syntheses of (+)-(RR)-48b'. The enantiomer (−)-(SS)-48b' was prepared by a different route from (−)-(SS)-136 (see below). Treatment of dimethyldiol (+)-(R)-25a' with dimethyl ditosylate (−)-(R)-25d' gave tetramethylcycle (+)-(RR)-48b'. Similarly, diol (−)-(S)-25a' and (+)-(S)-25d' gives (−)-(SS):48b'. The fact that the rotations of (+)-(RR)-48b' (see above) and (−)-(SS)-48b' (see below) are about equal in magnitude but opposite in sign indicates the compounds are optically pure.

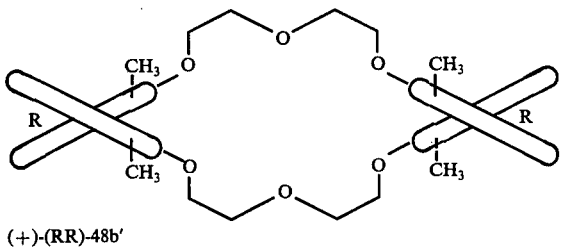

(+)-(RR)-48b'

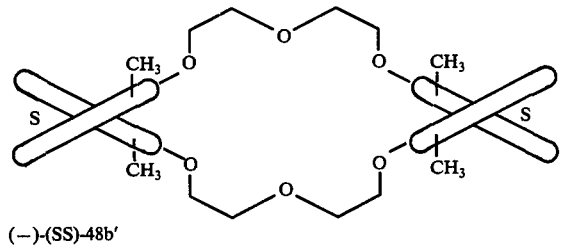

(−)-(SS)-48b'

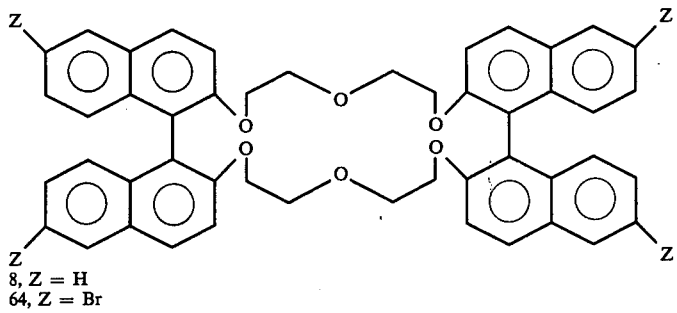

8, Z = H
64, Z = Br b 129, Z=CH$_2$CH$_2$OH or H, with one to four CH$_2$CH$_2$OH groups and zero to three H's.

Those compounds having substituents with Z=Br provided starting materials for compounds with other Z substituents. For example, (SR)-8 and (RR)-8 were brominated to give (SR)-64 and (+)-(RR)-64, respectively. Treatment in succession of (+)-(RR)-64 with butyllithium followed by ethylene oxide gave (RR)-129, a mixture of compounds with Z being either H or —CH₂CH₂OH, but with at least one CH₂CH₂OH. In the overall sequence, over half of the Br groups were converted to H by protonation by adventitious water of the aryllithium intermediate. The mixture thus produced was used to bind host to cross-linked chloromethylated polystyrene. Similarly, (−)-(SS)-64 and (SS)-129 are prepared.

(−)-(R)-128 with (−)-(R)-25d' gives (+)-(RR)-136. Lithiation of dibromomacrocyle (+)-(RR)-134 with butyllithium and treatment of the product with ethylene oxide gave a mixture of (+)-(RR)-8, (+)-(RR)-137, and (+)-(RR)-138 which were separated and each was characterized. Similarly, from (−)-(SS)-134, (−)-(SS)-137 and (−)-(SS)-138 are prepared. Similarly, from dibromodimethylmacrocycle (+)-(RR)-135 was obtained a mixture of (+)-(RR)-139 and (RR)-140 which were separated, but only the former was characterized. Similarly, from (−)-(SS)-135, (−)-(SS)-139 and (SS)-140 are prepared. Similarly, from dibromotetramethylmacrocycle (−)-(SS)-136 was obtained a mixture of (SS)-141, (SS)-142 and (−)-(SS)-48b'. The protonated

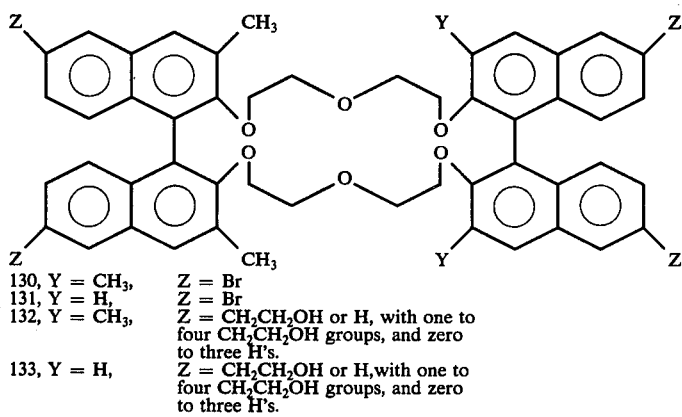

130, Y = CH₃,    Z = Br
131, Y = H,    Z = Br
132, Y = CH₃,    Z = CH₂CH₂OH or H, with one to four CH₂CH₂OH groups, and zero to three H's.
133, Y = H,    Z = CH₂CH₂OH or H, with one to four CH₂CH₂OH groups, and zero to three H's.

Similarly, (−)-(SS)-48b' is brominated to give (SS)-130 which is lithiated and the product treated with ethylene oxide to give (SS)-132. Similarly, (+)-(RR)-48B' is taken to (RR)-130 and thence to (RR)-132. Similarly, (+)-(RR)-48c is converted to (RR)-131 and thence to (RR)-133. Similarly (−)-(SS)-48c' is converted to (SS)-131 and thence to (SS)-133.

cycle (−)-(SS)-48b' was purified and characterized, and the mixture of ethoxylated cycles was purified and treated as a mixture. Similarly, from (+)-(RR)-136 is obtained a mixture of (RR)-141 and (RR)-142.

The CH₂CH₂OH groups of 129, 132, 133 and 137-142 provided points to attach the enantiomers of these compounds by the Williamson ether synthesis to chloro-

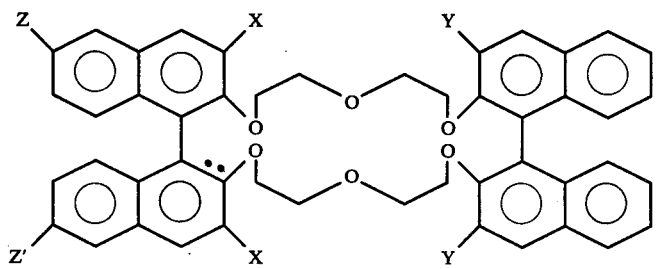

134, X=Y=H, Z=Z'=Br
135, X=CH₃, Y=H, Z=Z'=Br
136, X=Y=CH₃, Z=Z'=Br
137, X=Y=Z'=H, Z=CH₂CH₂OH
138, X=Y=H, Z=Z'=CH₂CH₂OH
139, X=CH₃, Y=Z'=H, Z=CH₂CH₂OH
140, X=CH₃, Y=H, Z=Z' CH₂CH₂OH
141, X=Y=CH₃, Z'=H, Z=CH₂CH₂OH
142, X=Y=CH₃, Z=Z'=CH₂CH₂OH

Treatment of dibromodiol (−)-(R)-127 with ditosylate (+)-(R)-1a and base gave dibromomacrocycle (+)-(RR)-134. Similarly, (+)-(S)-127 with (−)-(S)-1a gives (−)-(SS)-134. Treatment of dibromodimethyldiol (−)-(R)-128 with ditosylate (+)-(R)-1a and base gave dimethylcycle (+)-(RR)-135. Similarly, (+)-(S)-128 with (−)-(S)-1a gives (−)-(SS)-135. Treatment of dibromodimethyldiol (+)-(S)-128 with dimethylditosylate (+)-(S)-25d' and base gave (−)-(SS)-136. Similarly, methylated cross-linked polystyrene resin. The enantiomers of 137 and 139 were single compounds with single points of attachment. The enantiomers of the others contained several possible points of attachment. Although theoretically possible that a few molecules became covalently attached to the resin through more than one point (e.g., two point attachment), it is statistically improbable that more than one point was used by most of the molecules. Two point attachment would involve ring formation, and the chances are low that the spacing between two CH₂Cl groups in the resin and two CH₂CH₂OH groups on a host would match one another in position to react.

Amberlite XAD-2, a commercial copolymer of styrenedivinylbenzene, was chloromethylated to give about 15% of the aromatic rings chlormethylated. This material is referred to as 143.

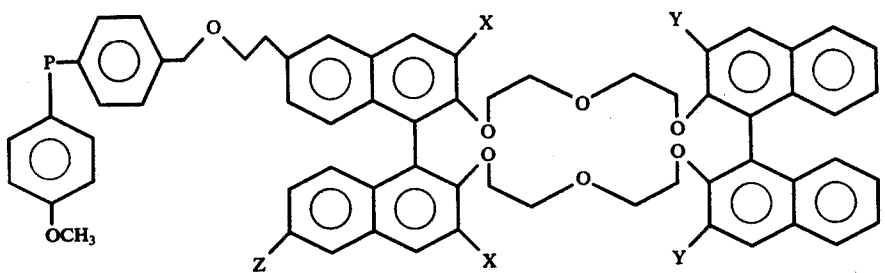

144, Z=X=Y=H, P=polystyrene polymer backbone
145, Z=Y=H, X=CH₃, P=polystyrene polymer backbone
146, Z=H or CH₂CH₂OH, X=Y=CH₃, P=polystyrene polymer backbone Treatment of a mixture of (+)-(RR)-137 and base with 143 gave product whose unused but sterically available CH₂Cl groups were capped by reflux with sodium methoxide to give grafted polymer, (RR)-144, Similarly, (SS)-144 is prepared from (−)-(SS)-137. Use of (+)-(RR)-139 in the same procedure gave (RR)-145. Similarly, (SS)-145 is formed from (−)-(SS)-139. Use of the mixture of (SS)-141 and (SS)-142 in the same procedure gave (SS)-146. Similarly, a mixture of (RR)-141 and (RR)-142 gives (RR)-146. The CH₂CH₂OH groups in 146 (unused to attach host to polymer) are rigidly positioned too far from the hole of the quest to affect its binding and chiral recognition properties.

$(CH_2)_4O$), and (−)-(S)-1, m.p. 207-208°, $[\alpha]_D^{25}$ −34.3°(C 1.0, $(CH_2)_4O$). The absolute configurations of these isomers are established (Tetrahedron, 27, 5999 (1971)) and are formulated both in a conventional and a more illustrative form, which will be used here and elsewhere. Although optically stable at 100° for 24 hours as a solution in dioxane-water, (−)-1 racemized 72% with HCl (∼1.2 N) present in the same solution at 100° for 24 hours, and 69% in butanol-0.67 M in potassium hydroxide at 118° for 23 hours. The optical stability of 1 and of its derived products are important to their uses.

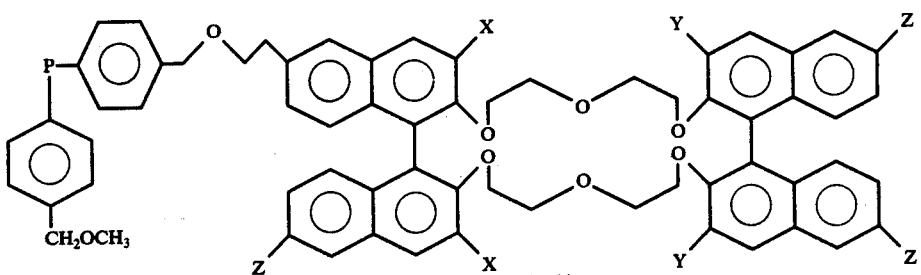

147, X=Y=H, Z=H or CH₂CH₂OH, P=polystyrene polymer backbone
148, X=Y=CH₃, Z=H or CH₂CH₂OH, P=polystrene polymer backbone
149, either X=CH₃ and Y=H or X=H and Y=CH₃, Z=H or CH₂CH₂OH, P=polystyrene polymer backbone Treatment of a mixture of (+)-(RR)-129 and base with polymer 143 gives after treatment of the product with sodium methoxide (RR)-147. Similarly, with (−)-(SS)-129, (SS)-147 is prepared. By use of (SS)-132 in the same procedure, (SS)-148 is prepared. Similarly from (RR)-132, (RR)-148 is prepared. Similarly, from (RR)-133, (RR)-149 is prepared. Similarly, from (SS)-133, (SS)-149, is prepared.

Experimental Part of Syntheses

General:

All temperatures are reported in degrees Centigrade (°C). In this section as before compounds will be referred to by number, and the structural formulas with their numbers will be placed close to the description of their synthesis. Since in many cases identical procedures will be applied to different starting materials, the procedures will be numbered sequentially so rational reference to them can be made.

Procedure 1.

Starting materials are described here. Racemic 2,2'-dihydroxy-1,1'-binaphthyl (1) was resolved as before [Tetrahedron Lett., 3617 (1971)] to give optically pure (+)-(R)-1, m.p. 207.5-208.5°, $[\alpha]_D^{25}$ +34.1°(C 1.0,

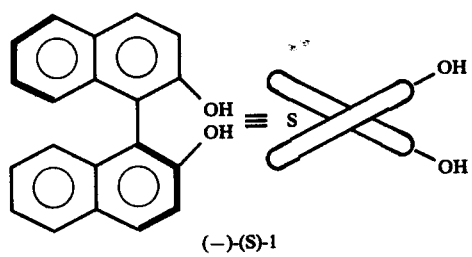

(−)-(S)-1

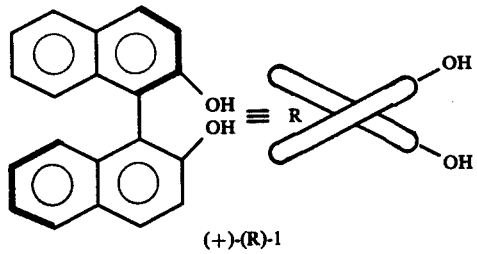

(+)-(R)-1

Procedure 2.

In this procedure, the synthesis of racemic 3,3'-dimethyl-2,2'-dihydroxy-1,1'-binaphthyl (25a') from racemic 2,2-dihydroxy-1,1'-binaphthyl (1) is described. The reaction sequence is as follows.

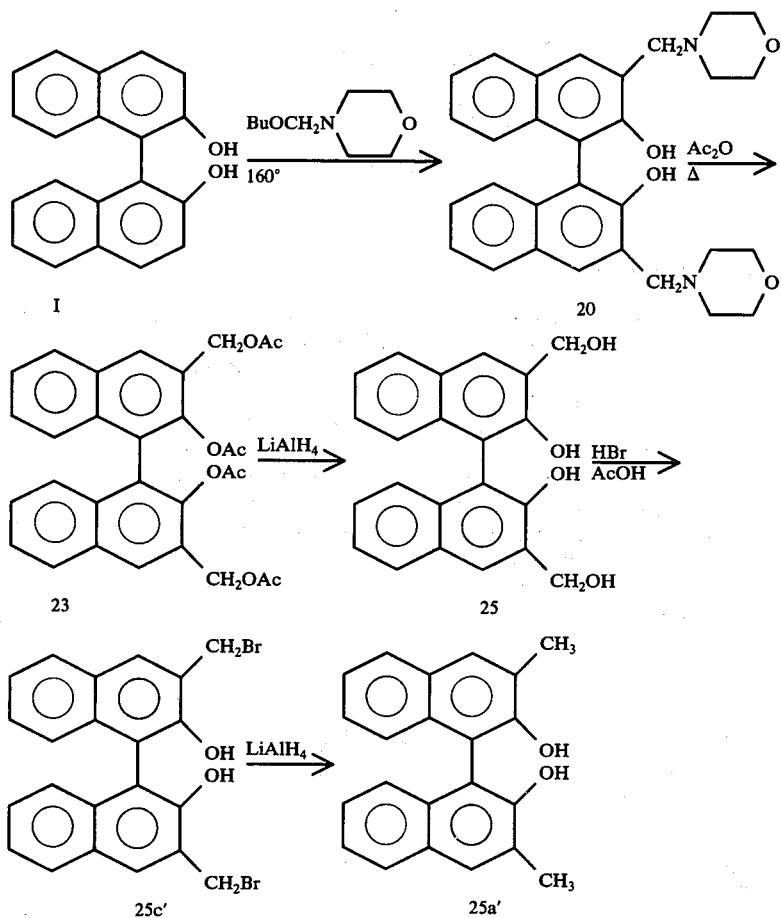

Compound 20 was produced from binaphthol 1 and 4-(n-butoxymethylene)morpholine [J. Chem. Eng. Data, 7, Pt. 2, 575 (1962)]. A solution of 100 g. (0.35 mole) of 1 in 850 g. (4.9 moles) of 4-(butoxymethylene)-morpholine was heated at 160° under nitrogen for 5 days (a precipitate of 20 started to form after 6 hours). The reaction mixture was cooled, 300 ml. of benzene was added with stirrings, and suspension stood at 25° for 10 hours. The solid was colllected, washed with 300 ml. of ether and dried at 25°(30 mm) to give 104 g. (61%) of 20. a sample of 5 g. of this material was crystallized from chloroform and ethyl acetate to give 4.5 of 20, m.p. 300° dec. The pmr spectrum (60 MHz) in CDCl$_3$ gave signals at δ 760 (m, ArH, 4H), 7.05 (m, ArH, 6H), 3.98 (AB guartet, J$_{AB}$=14Hz, ArCH$_2$N, 4H), 3.65 (m, OCH$_2$, 8H) and 2.60 (m, NCH$_2$, 8H). The base peak in the 70 eV mass spectrum was the molecular ion, m/e 484.

Anal. Calcd for C$_{30}$H$_{32}$N$_2$O$_4$: C, 74.36; H, 6.66; N, 5.78; Found: C, 74.23; H, 6.75; N, 5.66. Tetrol 25 was prepared from 20 as follows. A solution of 50 g. (105 mmol) of 20 in 1200 ml. of acetic anhydride was refluxed for 8 days. The solution was cooled, evaporated at 30 mm, and the residue was dissolved in 150 ml. of benzene. The product mixture was chromatographed in 1 Kg. of silica gel in hexane-benzene (2:1). Elution of the column with 1 l. hexane-benzene (2:1), 2 l. hexane-benzene (1:1), 5 l. benzene and 3 liters of 2% ether-benzene produced crude tetraacetate, 23. The combined fractions were evaporated, the residue was dissolved in 200 ml. of ether, which on concentration produced 24.5 g. (46%) of tetraacetate, m.p. 113°-114°.

Anal. Calcd for C$_{30}$H$_{28}$O$_8$: C, 70.03; H, 5.09. Found: C, 70.18; H, 5.18.

Reduction of the tetraacetate 23 gave 25 as follows.

To a refluxing suspension of 10.0 g. (210 mmol) of lithium aluminum hydride in 1.5 l. of dry ether was added dropwise 18.5 g. (36 mmol) of tetraacetate dissolved in tetrahydrofuran. The mixture was refluxed for 6 hours, cooled, and the excess reducing agent was destroyed by dropwise addition of ethanol at 0°. To the solution was added 400 ml. of 15% hydrochloric acid and 300 ml. of tetrahydrofuran. The solution was stirred for 12 hours, the organic layer was washed with water and 10% sodium bicarbonate solution, and dried over magnesium sulfate. The ether was evaporated at 30 mm and the concentrated solution (250 ml.) was refluxed with continuous replacement of the tetrahydrofuran by benzene. Tetrol 25 crystallized from the hot benzene solution to give 12.5 g. (98%), m.p. 222°-224°, reported [J. Orq. Chem., 29, 1394 (1964)] m.p. 231°. The base peak in the 70 eV mass spectrum was the molecular ion, m/e 346.

Anal. Calcd for C$_{22}$H$_{18}$O$_4$: C, 76.29; H, 5.24. Found: C, 76.44; H, 5.35.

Tetrol 25 was converted to dibromodiol 25c' as follows. A slow stream of dry hydrogen bromide was bubbled through a stirred suspension of 8.5 g. of tetrol 25 in 120 ml. acetic acid. After 10 minutes, the mixture became clear, the temperature increased, and a heavy precipitate formed. The HBr addition was stopped, the mixture was allowed to stand for one hour, the precipitate was collected, and the filtrate concentrated. The residue and precipitate were combined and dissolved in 500 ml. of ether, the solution was washed and water, and then with a saturated solution of sodium bicarbonate. The solution was dried and evaporated to give 11g. of solid. One recrystallization of this material from benzene gave 9.5 g. (85%) of white crystals of 25c', m.p. 215°–216°, pmr (100 MHz) in $CD_3COCD_3$, $\delta 8.05$ (s, $ArH^4$, 2H), 7.84 (q. $ArH^5$, 2H), 7.22 (m, $ArH^{8,7}$, 4H), 6.94 (m, $ArH^8$, 2H), 4.84 (s, $ArCH_2Br$, 4H), mass spectrum (70 eV) molecular ion m/e = 472.

Anal. Calcd for $C_{22}H_{18}O_2Br_2$: C, 55.96; H, 3.41. Found: C, 55.94; H, 3,53.

Finally, dibromide 25c'. To a suspension of 3 g. of $LiAlH_4$ in 350 ml. of dry ether was added 7.08 g. of 25c' in 100 ml. of tetrahydrofuran. The mixture was refluxed for 4 hours and stirred at 25° for 12 hours. At 0°, 25 ml. of 95% ethanol was added, followed by 300 ml. of 15% hydrochloric acid and 100 ml. of tetrahydrofuran. The layers were separated, and the organic layer was washed twice with 10% sodium bicarbonate solution, with water, and was dried and evaporated. The residue was crystallized from benzene to give 4.7 g. (98&) of 25a', m.p. 205°. The pmr spectrum (100 MHz) in $CDCl_3$ gave $\delta$ 7.76 (m, $ArH^{4,5}$, 4H), 7.17 (m,ArH, 6H), 5.05 (s, OH, 2H) and 2.47 (s, $CH_3$, 6H), and the mass spectrum (70 eV) gave a molecular ion at m/e = 314.

Anal. Calcd for $C_{22}H_{18}O_2$: C, 84.05; H, 5.77. Found: C, 83.98; H, 5.85.

Procedure 3

The optical resolution of racemic 25a' is described here.

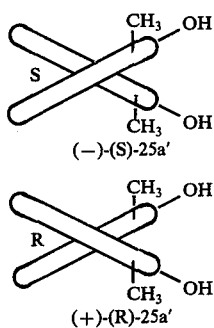

(−)-(S)-25a'

(+)-(R)-25a'

Racemic 25a' was resolved into its enantiomers as followed. A slurry of 146 g. of 25a', 750 ml. of dichloromethane and 84.5 g. of $POCl_3$ was stirred under nitrogen, and 111.3 g. of triethylamine was slowly added at a rate that maintained gentle reflux. After addition was complete, the solution was stirred an additional hour, and extracted twice with 300 ml. of water. The solution was dried, evaporated, and the crude chlorphosphate was stirred with 750 ml. of tetrahydrofuran and 200 ml. of water at 50° for one hour. To this solution, 700 ml. of ethyl acetate was added, the layers were separated, the organic layer was washed with 200 ml. of water, with 200 ml. of brine, dried with magnesium sulfate and evaporated under vacuum to produce white crystals of the phosphoric acid diester of 25a', weight 129 g. (75%), m.p >300°. This material gave a molecular ion in its mass spectrum (70 eV), m/e = 376.

A mixture of 60 g. of the above acid ester, 47 g. of cinchonine and 800 ml. of methanol was warmed to reflux, and to the solution was added 149 ml. of water. the solution was cooled to 25°, and the crystalline salt that separated was collected, washed and dried to give 40.8 g. of salt (38% yield based on racemate = 100%). This material was recrystallized from methanol-water three times to give 32g. of salt of constant rotation $[\alpha]^{578}_{25}$ −291°, $[\alpha]^{548}_{25}$ −339°, $[\alpha]_{438}{}^{25}$ −632°(C 1.1, dimethylformamide). The original mother liquors were evaporated to dryness to give a powder, 68.2 g. of salt of the other diastereomer, $[\alpha]_{436}{}^{25}$ +437° (C 1.0, dimethylformamide).

The (−)-salt (see above, 40 g.) was shaken with one liter of ether and 500 ml. of 5 M hydrochloric acid, and the resulting slurry was placed in a lighter than water refluxing extractor, until all white crystals dissolved (3 days) and for one extra day. The ether layer was dried and evaporated under vacuum to give a white foam, 21.5 g. (95% yield) of (−)-dieter acid, $[\alpha]_{578}{}^{25}$ −521°, $[\alpha]_{546}{}^{25}$ −604°, $[\alpha]_{436}{}^{25}$ −1120° (C 1, $CH_3OH$). This material was recrystallized from methanol-water to give constant melting diester acid, 20.7 g. (92%), $[\alpha]_{578}{}^{25}$ −561°, $[\alpha]_{546}{}^{25}$ −650°, $[\alpha]_{436}{}^{25}$ −1204° (C 1, $CH_3OH$).

The above (−)-diester acid (20.0 g.) was dissolved in 50 ml. of tetrahydrofuran and added dropwise to 2.9 g. of lithium aluminum hydride suspended in 200 ml. of dry tetrhydrofuran (a gentle reflux was maintained). The reaction mixture was allowed to stand 12 hours and was cautiously mixed with brine and diluted with ether. The organic layer was washed with saturated brine, dried and evaporated at reduced pressure to give 14.9 g. (90%) of white, crystalline diol, which was recrystallized from benzene. The product, 14.1 g. (85%) was fine white crystals of (+)-(R)-25a', m.p. 201.5°-203.5°, mass spectrum (70 eV) molecular ion m/e = 314, $[\alpha]_{578}{}^{25}$ + 30.3°, $[\alpha]_{546}{}^{25}$ + 37.1°, $[\alpha]_{436}{}^{25}$ + 104°(C 1.0, $CHCl_3$). The pmr spectrum of this material was identical to that of racemic 25a'.

Anal. Calcd for $C_{22}H_{28}O_2$: C, 84.05; H, 5.77; Found: C, 83.92; H, 5.82.

The powder from the mother liquors of the cinchonine salt were converted to the free diester acid (see above procedure), wt. 34.8 g., which was 73% optically pure (S)-material. To 30 ml. of hot ethanol was added 2.0 g. of this material and 1.77 g. of strychnine along with 22 ml of hot ethanol to give a tan solution. The solution was cooled, the salt that separated was collected, and recrystallized from methanol to constant rotation, weight 2.52 g. (60%), $[\alpha]_{578}$ + 322.6°, $[\alpha]_{546}$ + 371.4°, $[\alpha]_{436}{}^{25}$ +672° (C 0.5, $(CH_3)_2NCHO$). this material, 1.0 g., was converted to its free diester acid as with its enantiomer (see above), 0.47 g. (89%), $[\alpha]_{578}{}^{25}$ + 566°, $[\alpha]_{546}{}^{25}$ +869°, $[\alpha]_{436}$ + 1218° (C 1, $CH_3OH$). This rotation did not change when the material was recrystallized from methanol, mass spectrum (70 eV) molecule ion m/e=376. The compound (0.30 g.) was reduced with lithium aluminum hydride as with its enantiomer to give 0.224 g. (82%) of (−)-(S)-25a', m.p. 201°–203°, $[\alpha]_{578}{}^{25}$ −29.9°, $[\alpha]_{546}{}^{25}$ − 36.9°, $[\alpha]_{436}{}^{25}$ − 105° (C 1, $CHCL_3$), mass spectrum (70 eV) m/e=314.

Anal. Calcd for $C_{22}H_{18}O_2$: C, 84.05; H, 5.77; Found: C, 83.81; H, 5.79.

The absolute configurations of (+)- and (−):25a'λ were assigned on the basis of comparisons of the CD spectra of (+)-25a', (+)-(R):1 and (+)-(R)-2 described in application Ser. No. 448,333, p. 83. All three compounds exhibited a positive Cotton effect at ~315 nm.

Thus (+)-25a' possesses the (R)-, and (−)-25a' the (S)-configurations.

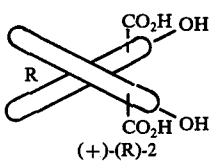

(+)-(R)-2

Procedure 4

The syntheses of 1a' and its two enantiomers are described here.

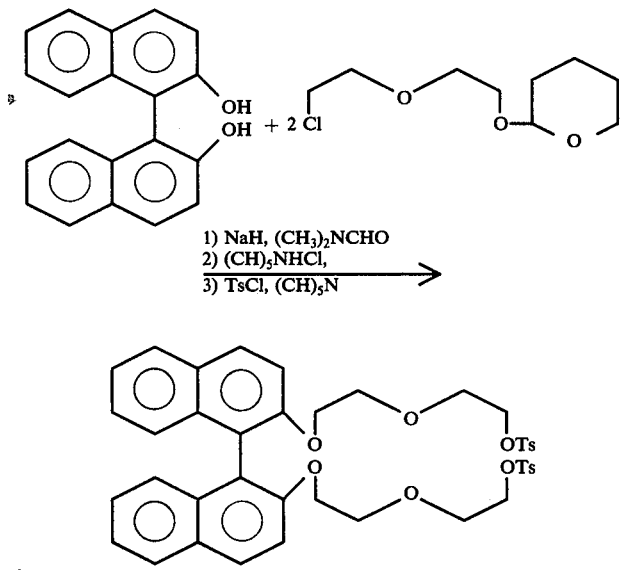

The preparation of racemic 1 a involved preparation of 2-(2'-chloroethoxy)ethyl 2'-tetrahydropyranyl ether as follows. To a stirred, boiling solution of 1.5 kg. (14.1 mol) of diethyleneglycol and 1.1 l. pyridine in 4.8 l. of benzene was added 450 g. (4.1 mol) of thionyl chloride over a period of 16 hours. The reaction mixture was refluxed with stirring for 17 hours, cooled and the two layers were separated. The lower layer was distilled, first to remove the pyridine and then to collect the crude chloroalcohol, b.p. 95°–105°at 20 mm.

This material was dissolved in 1.5 l of ether and extracted five times with 200 ml. portions of 3 N hydrochloric acid. The resulting solution was dried, concentrated, and the residue was distilled under vacuum to give 215 g (42% based on thionyl chloride) of 2-(2'-chloroethoxy)ethanol, b.p. 55°–60° at 5 mm. To 200 g. (1.61 mol.) of this chloroalcohol was added 202 g. of dehydropyran and one drop concentrated hydrochloric acid, whereupon an immediate exothermix reaction occurred. The reaction mixture was allowed to stand for 1 hour, and enough tribenzylamine was added to raise the pH from 5 to 6.5. The resulting solution was distilled under vacuum to give 322 g. (96%) of the tetrahydropyranyl ether as a colorless liquid b.p. 87°–88° at 0.5 mm.

Anal. Calcd for $C_9H_{17}ClO_3$: C, 51.79; H, 8.21. Found: C, 51.70; H, 8.32.

To a solution of 50.0 g. of 1 from Procedure 1 in one liter of dry dimethylformamide was added 19.5 g. of sodium hydride (50% oil dispersion). The mixture was heated to 70° with stirring under nitrogen. After one hour 2-(2'-cloroethoxy)-ethyl 2''-tetrahydropyranyl ether (see above for synthesis), 83.2 g. was added. The reaction mixture was stirred at 70° for 48 hours under nitrogen, cooled, and shaken with 2 liters of water. The mixture was extracted with dichloromethane, and the combined organic layers were washed with water, dried and evaporated. The residue in 1:1 pentane-dichloromethane was filtered through 250 g. of basic alumina, which was washed with additional solvent. The eluant was concentrated, and the oil was dissolved in 300 ml. of dichloromethane to which was added 150 ml. of methanol and 10 ml. of concentrated hydrochloric acid. The solution was stirred for 1 hour at 25°, neutralized with aqueous $NaHCO_3$, and the organic layer was separated and combined with dichloromethane washes of the aqueous layer. The organic layer was dried, evaporated, and the oil was washed with pentane to remove the mineral oil. The oil was dried at 90° at 0.1 mm to give 57.4 g. (70%) of diol as a gum. This material, 31.7 g., in 300 ml. of dry pyridine was cooled at −20°, and 30.0 g. of tosyl chloride was added in small portions during 15 minutes, during which time and for an additional 1.5 hours the mixture was cooled and stirred. After standing at −20° for 24 hours, the mixture was stirred into 1000 g. of ice. The water was decanted, and the residual oil was shaken with dichloromethane and 10% aqueous hydrochloric acid. The organic layer was washed with the same acid, then with 10% aqueous $NaHCO_3$, and water. The solution was dried evaporated at 25° under vacuum, and film dried at 0.01 mm (25°) to give 41.5 g. (75%) of 1a as a gum. The 100 MHz pmr spectrum in $CDCl_3$ gave signals at δ7.7 (m, ArH, 8H), 7.2 (m, ArH, 12H), 3.95 (m, $CH_2$, 4H), 3.61 (m, $CH_2$, 4H), 3.30 (m, $CH_2$, 4H), 2.95 (m, $CH_2$, 4H) and 2.35 (s, $CH_3$, 6H).

Anal. Calcd for $C_{42}H_{42}O_{10}S_2$: C, 65.44; H, 5.49; Found: C, 65.64; H, 5.36.

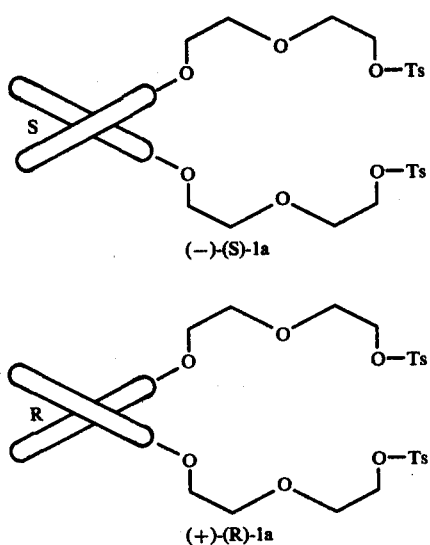

(−)-(S)-1a (+)-(R)-1a

The same procedure was applied to the synthesis of (−)-(S)-1a from optically pure (−)-(S)-1 (from Procedure 1) as was used to prepare 1a. The (−)-(S)-1a produced (80% yield) possessed a pmr (100 MHz) spectrum identical to 1a, $[\alpha]_D^{25} - 30.7°$ (C 1, $(CH_2)_4O$).

Anal. Calcd for $C_{42}H_{42}O_{10}S_2$: C, 65.44; H, 5.48; Found: C, 65.36; H, 5.59.

Similarly (+)-(R)-1a was prepared in 78% yield from optically pure (+)-(R)-1 (Procedure 1), and possessed a pmr (100 MHz) spectrum identical to 1a, $[\alpha]_D^{25} +$ 31.0°(C 1, $(CH_2)_4O$).

Anal. Calcd for $C_{42}H_{42}O_{10}S_2$: C, 65.44; H, 5.48; Found: C, 65.64; H, 5.37.

Procedure 5

The syntheses of 25d' and its enantiomers are described.

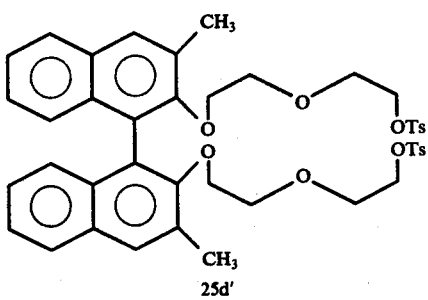

25d'

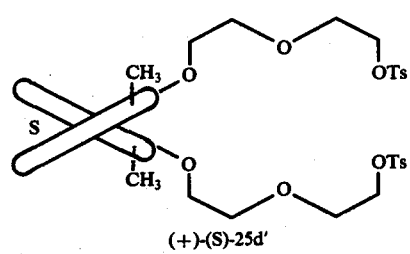

(+)-(S)-25d'

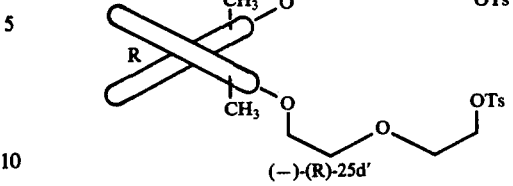

(−)-(R)-25d'

The synthesis of 25d' from racemic 25a' (from Procedure 2) is described, and the procedure used is the same as that described under Procedure 4 for the conversion of diol 1 to ditosylate 1a'. From 25a', 3,3'-dimethyl-2,2'-bis(diethylenozytetrahydropyran)-2,2'-binaphthyl was produced as an oil in 65% yield. This bis-pyranyl ether was cleaved with acid to give the corresponding diol as an oil in 90% yield. This material was tosylated to give 25d' as a glass in 90% yield. The pmr spectrum of this material (100 MHz) in $CDCl_3$ gave δ 7.70 (m, ArH, 8H), 7.28 (m, ArH, 6H), 7.05 (q, ArH, 4H), 3.86 (q, $CH_2OTs$, 4H), 3.49 (m, $OCH_2CH_2OTs$, 4H), 3.10 (m, $ArOCH_2CH_2O$, 8H), 2.46 (s, $CH_3$-naphthyl, 6H) and 2.37 (s, $CH_3C_6H_4$, 6H).

Anal. Calcd for $C_{44}H_{46}O_{10}S_2$: C, 66.15; H, 5.80; Found: C, 66.40; H, 6.16.

Similar treatment of optically pure (−)-(S)-25a' (from Procedure 3) gave (+)-(S)-25d' in yield 72% yield by Procedure 4, $[\alpha]_{578}^{25} + 69.320$ (C 1, $CHCl_3$), whose pmr spectrum (100 MHz) was identical to that of racemic 25d'.

Anal. Calcd for $C_{44}H_{46}O_{10}S_2$: C, 66.15; H, 5.80; Found: C, 66.16; H, 5.91.

Similar treatment of optically pure (+)-(R)-25a' (from Procedure 3) gave (−)-(R)-25d' in 63% yield by Procedure 4, $[\alpha]_{578}^{25} - 69.7°$ (C 1, $CHCl_3$), whose pmr spectrum (100 MHz) was identical to that of racemic 25d'.

Anal. Calcd for $C_{44}H_{46}O_{10}S_2$: C, 66.15; H, 5.80; Found: C, 66.01; H, 5.92.

Procedure 6

The syntheses of the optically pure multiheteromacrocycles, (−)-(SS)-8 and (+)-(RR)-8, are described in this section.

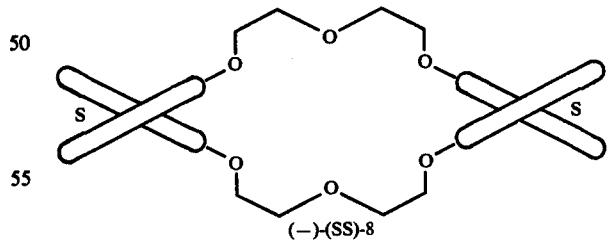

(−)-(SS)-8

A solution of 14.5 g. (35.0 mmol.) of diethyleneglycol ditosylate in 150 ml. of tetrahydrofuran was added during 10 minutes to a boiling solution of a mixture of 10.0 g. (35.0 mmol.) of optically pure diol (−)-(S)-1 (from Procedure 1) and 8 g. of potassium t-butoxide in 250 ml. of tetrahydrofuran and 2 ml. of water. The resulting mixture was refluxed for 12 hours, cooled, neutralized with concentrated hydrochloric acid and filtered. The filtrate was concentrated and chromatographed on 1 kg.

of neutral alumina with benzene-ether (9 to 1, v/v) as eluting solvent, cut in one liter fractions. Fractions 2–4 contained only (−)-(SS)-8 (3.9 g.), whereas fractions 5–14 contained mixtures of (−)-(SS)-8 and of cycle (+)-(S)-4, (2.0 g.). By fractional recrystallization of the mixture from benzene-cyclohexane and combining appropriate fractions, 4.3 g. of white needles of (−)-(SS)-8 were obtained as a solvate of 0.5 mole of benzene and 0.5 mole of cyclohexane, as shown by integration of the substance's pmr spectrum (100 MHz), m.p. 123°–126°.

Anal. Calcd for $C_{48}H_{40}O_6 \cdot 0.5C_6H_{12} \cdot 0.5C_6H_6$: C, 81.69; H, 6.22. Found: C, 81.71;

The solvate was heated at 170° at 50 $\mu$ for 17 hours to give 3.9 g. (31%) of pure (−)-(SS)-8 as a colorless glass, $[\alpha]_{578}^{25} - 220°$, $[\alpha]_{546}^{25} - 262°$, $[\alpha]_{436}^{25} - 599°$ (C 1.10, $CH_2Cl_2$). The rotations of this substance were the same before and after heating at 170° when correction was made for the presence of the solvate. The base peak in the mass spectrum (70 eV) was that of the molecular ion, m/e 712. From the filtrates of the fractional recrystallizations of (−)-(SS)-8 was isolated by fractional sublimation, 0.24 g. (2%) of (+)-(S)-4, m.p. 131°–132°, $[\alpha]_{578}^{25} + 72°$, $[\alpha]_{548}^{25} + 78°$, $[\alpha]_{436}^{25} + 40°$ (C 0.88, $CH_2Cl_2$). The base peak in the mass spectrum (70 eV) was that of the molecular ion at m/e 356.

Anal. Calcd for $C_{24}H_{20}O_3$: C, 80.88; H, 5.66; Found: C, 80.81; H, 5.55.

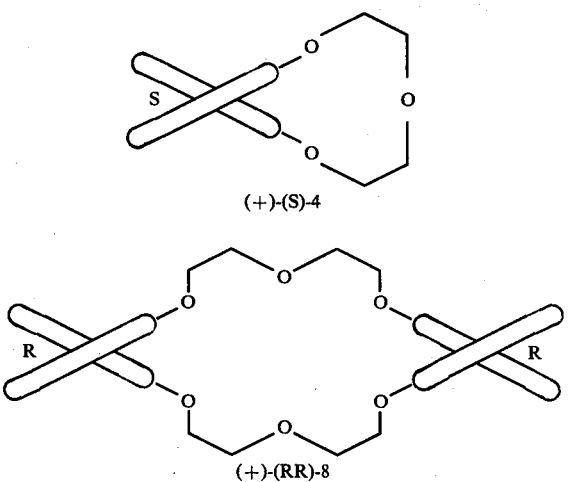

By the same procedure, optically pure diol (+)-(R)-1 (from Procedure 1) and diethyleneglycol ditosylate gave (+)-(RR)-8 as a glass in 22% yield, $[\alpha]_{578}^{25} + 221°$ (C 1, $CH_2Cl_2$). As with its enantiomer, the compound crystallized as a solvate of 0.5 mole of benzene and 0.5 mole of cyclohexane, as shown by integration of the substance's pmr spectrum (100 MHz), m.p. 123°–126°. The compound was dried at 170° at 20 microns, and analyzed as a gum.

Anal. Calcd for $C_{48}H_{40}O_6$: C, 80.88; H, 5.66; Found: C, 80.79; H, 5.43.

Compounds (−)-(SS)-8 and (+)-(RR)-8 also formed a storable solvate of carbon tetrachloride (needles) when crystallized from that solvent.

Optically pure (−)-(SS)-8 and (+)-(RR)-8 or properties identical to those described above were prepared by alternate routes described as follows.

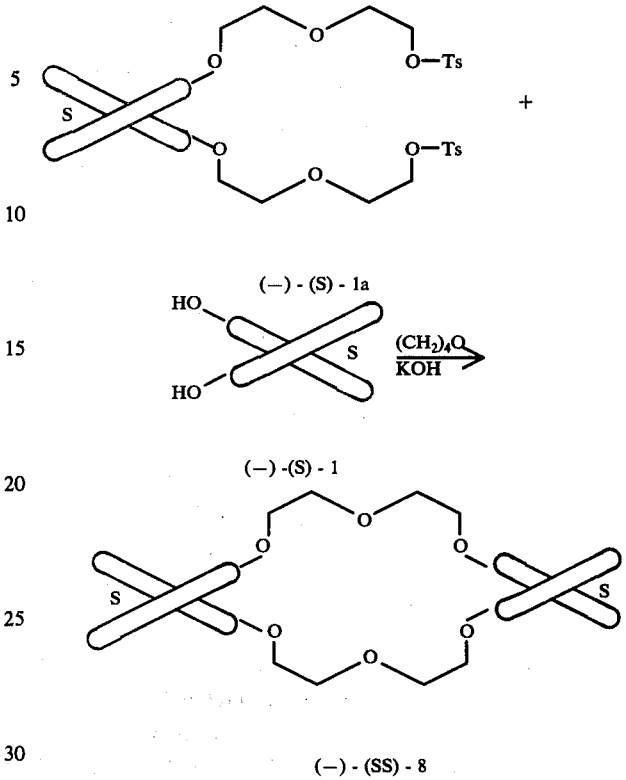

To a solution of 15.4 g. (0.54 mole) of optically pure (−)-(S)-1 (from Procedure 1) in one liter of tetrahydrofuran was added 7.15 g. (0.108 mole) of potassium hydroxide (85%) dissolved in 50 ml. of water. The solution was refluxed under positive nitrogen pressure for 1 hour and 41.5 g. (0.54 mole) of optically pure (−)-(S)-1a (from Procedure 4) in 250 ml. of tetrahydrofuran was added. The resulting light orange solution was refluxed for 50 hours, concentrated to 150 ml. (under vacuum), and shaken with a mixture of dichloromethane and water. The aqueous phase was washed with two 150 ml. portions of dichloromethane. The combined organic phases were washed with several equal volumes of 10% aqueous potassium hydroxide and with water. The solution was dried with magnesium sulfate and the solvent was evaporated to give 40.0 g. of a dark brown oil. This material was chromatographed on 850 g. of silica gel, and eluted in 500 ml. fractions with dichloromethane. The (−)-(SS)-8 was obtained by evaporation of fractions 4–6, and was crystallized from a mixture of 1:2 benzene-cyclohexane to give 16.2 g. of the solvate, as white needles, m.p. 123°–124°. When heated to 170° at 0.06 mm. for 10 hours, (−)-(SS)-8 was obtained (14.0 g. or 37% yield) as a transparent glass, $[\alpha]_{576}^{25} -220.0°$ (C 1, $CH_2Cl_2$), and it possessed the same mass and pmr spectral properties as the same compound reported above.

Similarly, optically pure (+)-(R)-1a and (+)-(R)-1 gave (+)-(RR)-8 as a transparent glass in 30% yield, $[\alpha]_{576}^{25} +219°$ (C 1, $CH_2Cl_2$). The substance possessed the same mass and pmr spectral properties as the same compound reported above.

Procedure 7

The syntheses of optically pure multiheteromacrocycles, (+)-(SS)-48c′ and (+)-(RR)-48c′ are described in this section. In patent application Ser. No. 448,333 on page 160 is described the first synthesis, analysis and description of the physical properties of (+)-(SS)-48c′, and on page 164a is described the first synthesis, analysis and description of the properties of optically pure (+)-(RR)-48c′. The latter synthesis clearly established the abosolute configuration of (+)-(RR)-48c′ (and its enantiomer), since the absolute configurations of the two halves of the molecule that served as starting materials were both known to possess the (R)-configuration. Newer and more direct syntheses are described here.

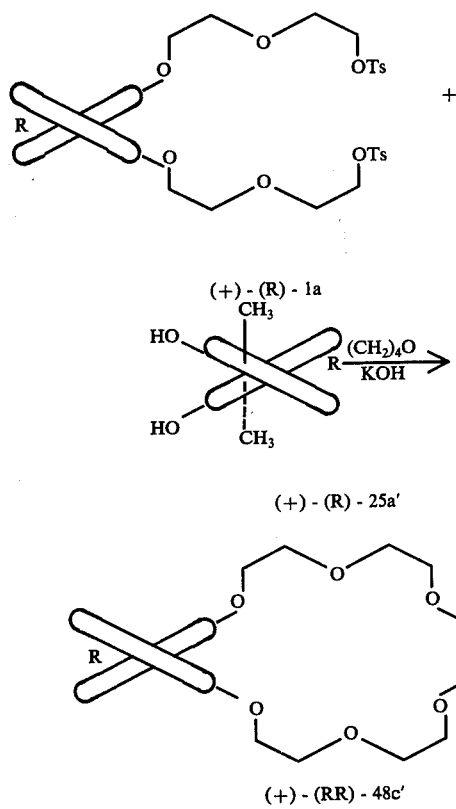

The general method is illustrated by the conversion of optically pure ditosylate (+)-(R)-1a (from Procedure 4) and optically pure diol (+)-(R)-25a′ (from Procedure 3) to optically pure (+)-(RR)-48c′. To 200 ml. of dry tetrahydrofuran under nitrogen was added 1.0 g. of dimethyldiol (+)-(R)-25a′ and 0.45 g. of 85% potassium hydroxide. The mixture was brought to reflux, and 2.40 g. of (+)-(R)-25a′ dissolved in 50 ml of dry tetrahydrofuran was added. The reaction mixture was refluxed under nitrogen for 170 hours, cooled, evaporated under vacuum, and the resulting oil was shaken with 100 ml. of dichloromethane and 75 ml. of water. The organic layer was washed with water, brine, dried and evaporated to a thick brown oil. This oil was dissolved in a minimum amount of dichloromethane, and the solution was filtered with washing (CH$_2$Cl$_2$) through a 50 g. plug of basic alumina to yield on evaporation of the eluate a tan foam. This material was chromatographed on 10 g. of neutral alumina and eluted with absolute ether. The pure product was eluted with absolute ether, evaporation of which under vacuum gave 1.51 g. (64%) of a white foam, (+)-(RR)-48c′, mass spectrum (70 eV) molecular ion m/e = 740, [α]$_{578}^{25}$ + 152°, [α]$_{546}^{25}$ + 170.2°, [α]$_{436}^{25}$ 30 378° (C 1, CHCl$_3$). The 100 MHz pmr spectrum was identical to that of the same material prepared previously (Serial No. 448,333, page 164a).

Anal. Calcd for C$_{50}$H$_{44}$O$_6$: C, 81.05; H, 5.99. Found: C, 80.76; H, 6.04.

The same procedure applied to alternate starting material also gave (+)-(RR)-48c′.

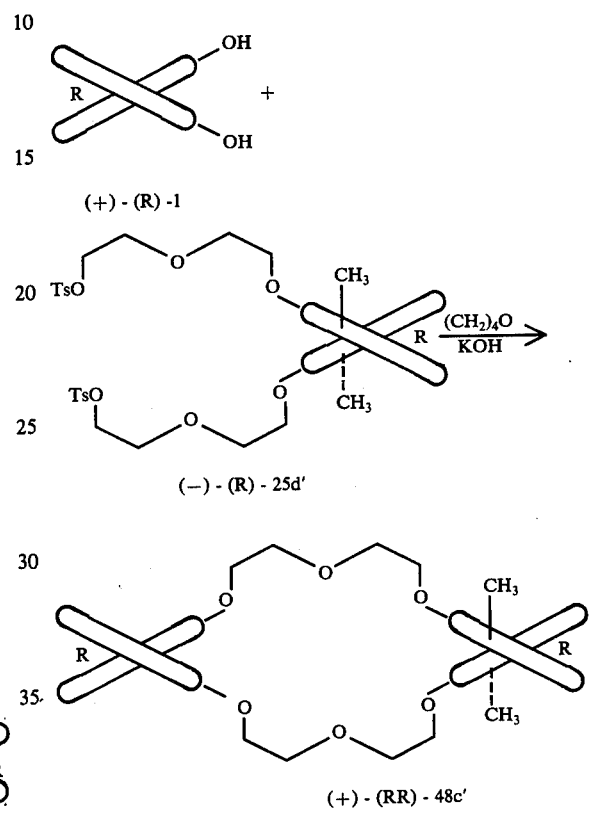

To 6.04 g. of optically pure (+)-(R)-1 (from Procedure 1), 16.84 g. of optically pure (−)-(R)-25d′ (from Procedure 5) and 2.80 g. of 85% potassium hydroxide was applied the above cyclization procedure. Isolated was 9.94 g. (63%) of optically pure (+)-(RR)-48c′, [α]$_{578}^{25}$ + 151° (C 1, CHCl$_3$). This material possessed the same mass spectral and pmr properties as the same material prepared above.

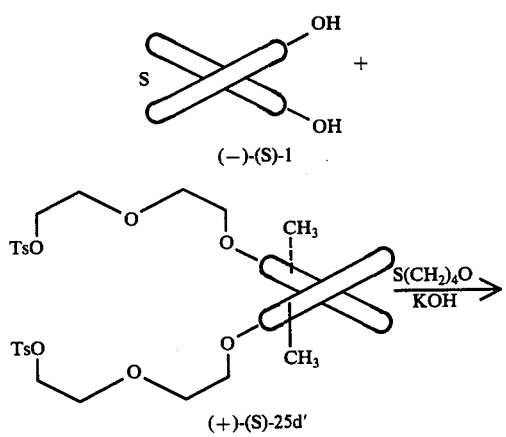

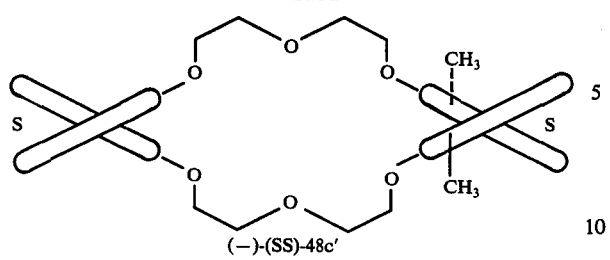

(−)-(SS)-48c′

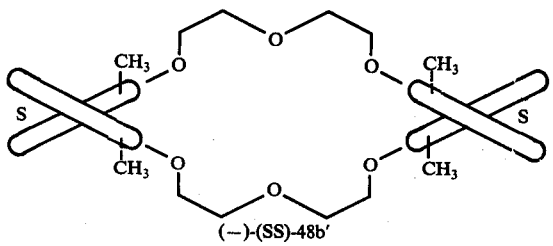

(−)-(SS)-48b′

The same method was applied to the synthesis of (−)-(SS)-48c′ from optically pure (−)-(S)-1 (from Procedure 1) and optically pure (+)-(S)-25d′ (from Procedure 5) to give a 58% yield of optically pure products of the same mass and pmr spectral properties as was obtained for (SS) (RR)-48c′ (racemic 48c′) (Ser. No. 448,333, page 160), $[\alpha]_{578}^{25}$ − 149° (C 1, CHCl$_3$).

Anal. Calcd for $C_{50}H_{44}O_6$: C, 81.05, H, 5.99; Found: C, 81.38; H, 6.02.

Procedure 8

The synthesis of the optically pure multiheteromacrocycle, (+)-(RR)-48b′, is described for the first time here. The syntheses of racemic and meso compounds, (SS) (RR)-48b′ and (SR)-48b′ respectively, were reported in Ser. No. 448,333, page 158.

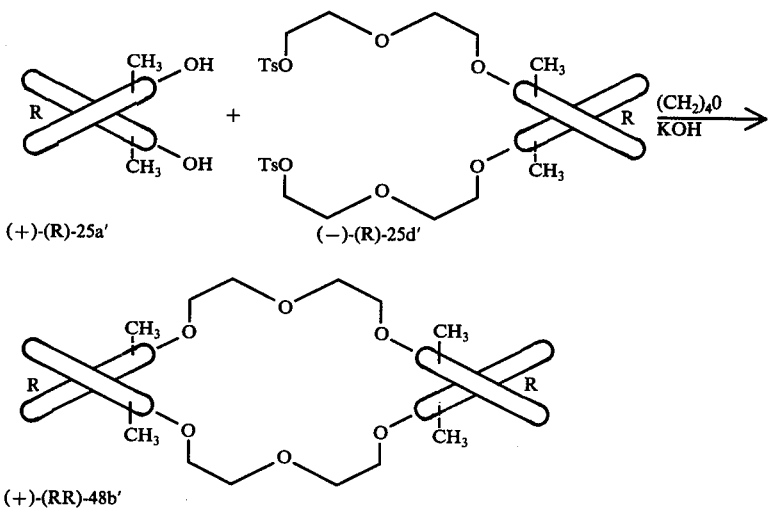

Optically pure dimethyldiol (+)-(R)-25a′ (from Procedure 3) and optically pure dimethylditosylate (−)-(R)-25d′ (from Procedure 5) were treated wih potassium hydroxide in dry tetrahydrofuran by the same general method reported above in Procedure 7 except that the reflux period of the reaction was extended to 231 hours. Optically pure (+)-(RR)-48b′ was isolated as a foam in 25% yield, gave a mass spectrum (70 eV) with a molecular ion at m/e = 769, and a pmr spectrum (100 MHz) in CDCl$_3$ with δ 7.70 (m, ArH $^{4,5}$, 8H), 7.2 (m, ArH, 12H), 3.50 (m, CH$_2$O, 8H), 2.92 (m, CH$_2$O, 8H), 2.45 (d, CH$_3$, 12H), $[\alpha]_{578}^{25}$ + 135°, $[\alpha]_{536}^{25}$ + 157°, $[\alpha]_{436}^{25}$ + 321° (C 1, CHCl$_3$).

Anal. Calcd for $C_{52}H_{48}O_6$: C, 81.23; H, 6.28; Found: C, 80.84; H, 6.24.

The enantiomer, (+)-(SS)-48b′, was prepared by a different method described under Procedure 12.

Procedure 9

The syntheses of the dibromodiols, (−)-(R)-127, (+)-(S)-128 and (−)-(R)-128, are reported here.

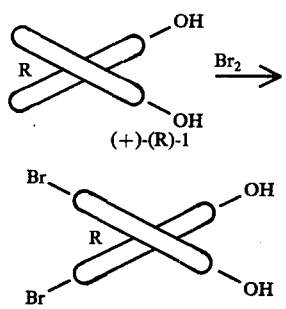

(−)-(R)-127

In 40 ml. of dichloromethane, 2.10 g. (7.34 mmole) of optically pure (+)-(R)-1 (from Procedure 1) was dissolved and the system cooled to -75° C in a dry ice-acetone bath. Bromine, 1 ml. or 19.6 mmole was added dropwise over a period of 20–30 minutes with constant stirring. The solution was stirred for an additional 2.5 hours while the flask was allowed to warm to 25°. After an additional 30 minute-stirring at 25°, the excess bromine was destroyed by addition of 50 ml. of 10% aqueous solution of sodium bisulfite. The two layers were separated and the organic layer was washed with saturated sodium chloride solution and dried. Evaporation of the solution gave 3.6 g. of solid which was recrystallized from benzene-cyclohexane to give 3.20 g. (99% yield) of the desired product. When the reaction was repeated using 18.0 g. of (+)-(R)-1 in 400 ml. of dichloromethane and 9.0 ml. (176.4 mmole) of bromine in 50 ml. of dichloromethane, the final product was obtained in 94% yield. The ¹H nmr (T 60-D, CDCl₃-TMS) showed the following absorptions: δ: 5.07 (s, OH, 2 H); 6.85 (d, ArH-8, $J_{7,8}$ = 9 Hz, 2 H); 7.15 (d, ArH-3, $J_{4,3}$ = 9 Hz, 2 H); 7.25 (d of d, $J_{7,8}$ = 9 Hz, $J_{5,7}$ = 2 Hz, 2 H); 7.75 (d, ArH-4, $J_{3,4}$ = 9 Hz, 2 H); 7.90 (d, ArH-5 $J_{5,7}$ = 2 Hz, 2 H). The compound gave $[\alpha]_{578}^{25}$ − 129° (C 1, CH₂Cl₂).

Anal. Calcd for C₂₂H₁₆O₂Br₂: C, 55.92; H, 2.54; Found: C, 55.81 H, 2.50.

Procedure 10

The syntheses of the optically pure dibromocycles (+)-(RR)-134, (+)-(RR)-135 and (−)-(SS)-136 are reported here.

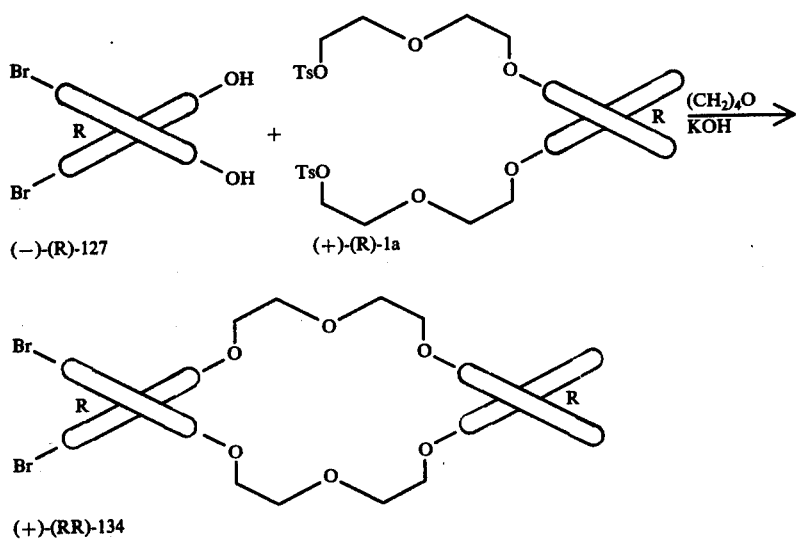

Anal. Calcd. for C₂₀H₁₂O₂Br₂: C, 54.05; H, 2.70; Br, 36.04; Found: C, 54.00; H, 2.75; Br, 35.92.

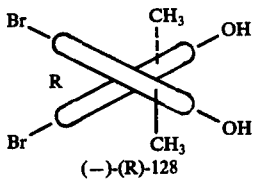

When optically pure dimethyldiol (+)-(R)-25a' (from Procedure 3) was subjected to the same procedure except the reaction temperature was -50° instead of -75°, (−)-(R)-128 was produced in 90% yield as a glass, $[\alpha]_{578}^{25}$ − 68° (C 1.4, CH₂Cl₂).

Anal. Calcd for C₂₂H₁₆O₂Br₂: C, 55.92; H, 2.54; Br, 33.90; Found: C, 55.80; H, 2,48; Br, 34.06.

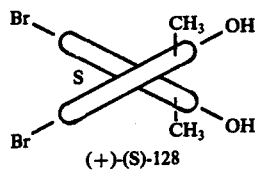

Application of the same bromination procedure to optically pure dimethyldiol (−)-(S)-25a' gave (+)-(S)-128 in 88% yield as a glass, $[\alpha]_{578}^{25}$+68.2° (C 1, CH₂Cl₂).

In 400 ml. of dry tetrahydrofuran, 10.3 g. or 23.2 mmole of optically pure (−)-(R)-127 (from Procedure 9) was dissolved and stirred under nitrogen for about 10 minutes. Then potassium hydroxide pellets (2.88 g.) were added and the solution was refluxed for 4 hours after which all the solid went into solution. Next, 18 g. (23.3 mmole) of the optically pure ditosylate (+)-(R)-1a, dissolved in 50 ml. of tetrahydrofuran, was added dropwise, and refluxing was continued for a total of 17 hours. The reaction mixture was cooled, filtered and the solids were washed with chloroform. The washings and the filtrate were combined, dried and evaporated to give a viscous oil (21.9 g.). Chromatography of the oil on 500 g. of neutral alumina with 2 liters of dichloromethane gave 17 g. of a white foam. This material was crystallized and recrystallized three times from 2:1 benzene-cyclohexane, to give a solvate, m.p. 136°-137°. Removal of the solvent at 80° in vacuo (0.1 mm Hg) gave a glassy material, 15.0 g. or 74% yield, which had the following ¹H nmr (T 60-D, CDCl₃-TMS): δ 3.20 (m, CH₂O-CH₂, 8 H); 3.80 (m, ArOCH₂, 8 H); 6.80 (d, Br-ArH-8, $J_{7,8}$ = 9 Hz, 2H); 7.08 (m, ArH, 8 H); 7.13 (d of d, Br-ArH-7, $J_{7,8}$ = 9 Hz, $J_{5,7}$ = 2 Hz, 2 H); 7.18 (d, Br-ArH-3, $J_{3,4}$ = 9 Hz, 2 H); 7.75 (d, ArH-4, $J_{3,4}$ = 9 Hz, 4 H); 7.80 (d, ArH-3, $J_{3,4}$ = 9 Hz, 2 H); 7.90 (d, Br-ArH-5, $J_{5,7}$ = 2 Hz, 2 H). The specific rotation on the solvent-free material, (+)-(RR)-134, was found to be $[\alpha]_{589}^{25}$ + 157°, $[\alpha]_{578}^{25}$ + 166° (C = 1.0, CH₂Cl₂).

Anal. Calcd. for C₄₈H₃₆O₆Br₂: C, 66.21; H, 4.37; Br, 18.39. Found: C, 65.90; H, 4.42;

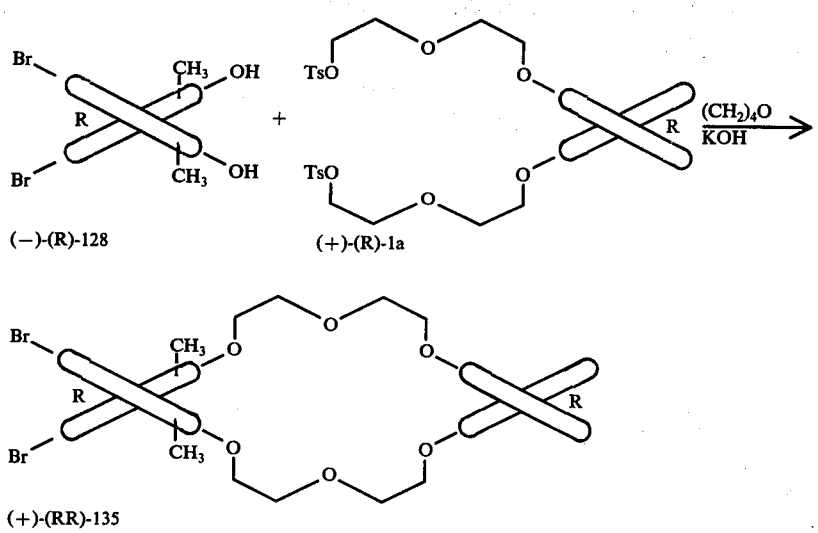

(−)-(R)-128    (+)-(R)-1a (+)-(RR)-135

Similarly from optically pure dibromodimethyldiol, 10.24 g. (−)-(R)-128 (from Procedure 9) and optically pure ditosylate (+)-(R)-1a, 15.1 g., (from Procedure 4) was prepared 12.1 g., (69%) of (+)-(RR)-135; m.p. 135°-143° (benzene-cyclohexane solvate). Before crystallization from benzene-cyclohexane, the reaction product was chromatographed on 600 g. of neutral alumina with dichloromethane as eluting agent. After drying at 160° and 0.01 mm. pressure, the material gave $[\alpha]_{578}^{25}$ + 172° (C 1.1, $CH_2Cl_2$).

Anal. Calcd. for $C_{50}H_{42}O_6Br_2$: C, 66.82; H, 4.68; Br, 17.82; Found: C, 66.58; H, 4.70; Br, 18.02 product was first subjected to neutral alumina chromatography and then gel permeation chromatography (100A styragel) to give 13% of (−)-(SS)-136 as a white foam, $[\alpha]_{589}^{25}$ − 113.4°, $[\alpha]_{546}^{25}$ − 133.2°, $[\alpha]_{436}^{25}$ − 267° (C 1.0, $CHCl_3$), pmr (100 MHz in $CDCl_3$), δ: 2.45 (s, $CH_3$, 12H); 3.0 - 3.4 (m, $ArCH_2CH_2$, 8H) 3.55 - 3.85 (m, $ArOCH_2$, 8H); 6.7 - 7.4 (m, ArH, 8 H); 7.6- 8.0 (m, ArH, 8 H).

Anal. Calcd. for $C_{52}H_{46}Br_2O_6$: C, 67.39; H, 5.00; Found: C, 67.34; H, 5.30.

Procedure 11

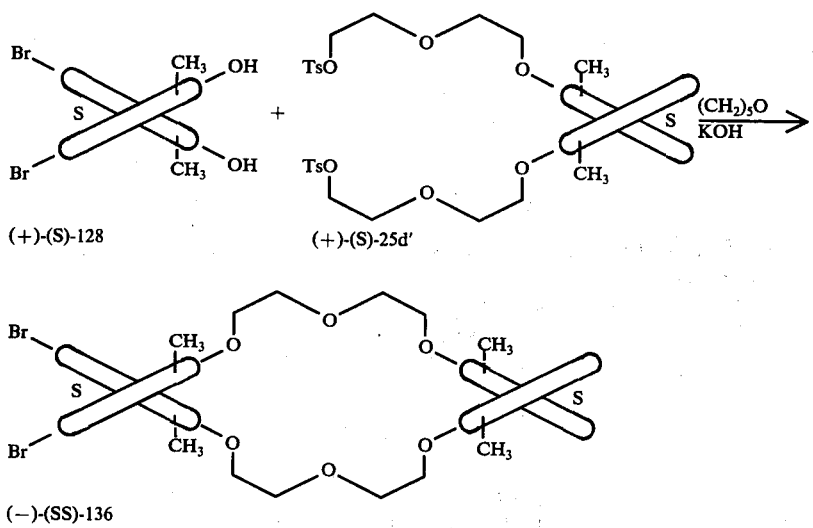

(+)-(S)-128    (+)-(S)-25d'

(−)-(SS)-136

Similarly from optically pure dibromodimethyldiol, (+)-(S)-128 (from Procedure 9) and optically pure dimethylditosylate (+)-(S)-25d' (from Procedure 5) was prepared optically pure dibromotetramethyl cycle (−)-(SS)-136. The reaction was run for 168 hours. The The syntheses of tetrabromocycles (SR)-64 and optically pure (+)-(RR)-64 are reported here. The former two compounds are reported in application Ser. No. 448,333, page 167.

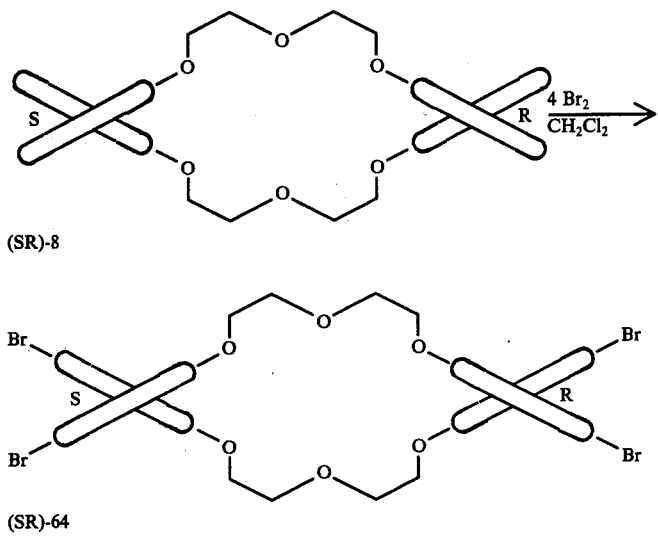

(SR)-8

(SR)-64

In 50 ml. of dichloromethane, 2.00 g. (2.80 mmole) of (SR)-8 was dissolved, and the solution was cooled to -5°. With stirring, 1.0 ml. (19.6 mmole) of bromine dissolved in 20 ml. of dichloromethane was added dropwise over a period of 40 minutes. The mixture was stirred at -5° for 12 hours, and the excess bromine was destroyed by addition of 50 ml. of 10% sodium bisulfite solution. The clear, colorless organic layer was separated and warmed over solid potassium carbonate. The mixture was then filtered, and the filtrate was evaporated to give a white powder that was recrystallized from chloroform - heptane to give 2.60 g. (91%) of (SR)-64, m.p. 334°-335°. The mass spectrum (70 eV) gave a molecular ion at m/e = 1024.

Anal. Calcd for $C_{48}H_{36}O_6Br_4$: C, 56.03; H, 3.50; Br, 31.13; Found: C, 56.30; H, 3.50; Br, 31.10.

By the same procedure, optically pure (+)-(RR)-8 (from Procedure 6) was brominated to give optically pure (+)-(RR)-64 in 91% yield, m.p. 189°-191° (from dichloromethanepentane), $[\alpha]_{578}^{25}$ + 124° (C 1.86, $CHCl_3$).

Anal. Calcd. for $C_{48}H_{36}O_6Br_4$: C, 56.03; H, 3.50; Br. 31.13. Found: C, 56.02; H, 3.42; Br, 31.17.

Procedure 12

This section reports the lithiation and ethoxylation of the organometallic produced to give cycles with hydroxyethyl groups attached. The procedure is illustrated with optically pure dibromodimethylcycle (+)-(RR)-135 (from Procedure 10), as starting material and optically pure mono and diethoxylated cycles (+)-(RR)-139, (+)-(RR)-140 respectively, and protonated cycle (+)-(RR)-48c' as products.

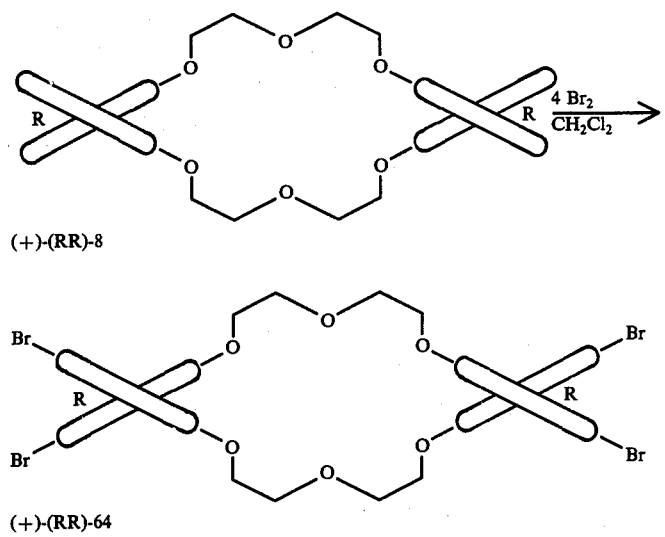

(+)-(RR)-8

(+)-(RR)-64

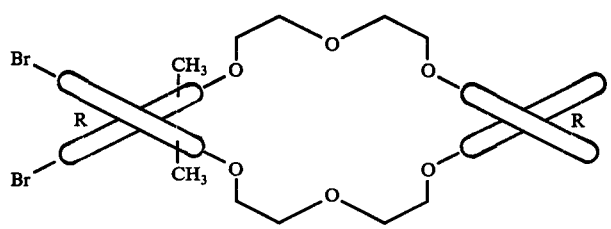

(+)-(RR)-135

1) BuLi, CH$_3$OCH$_2$CH$_2$OCH$_3$, −75°
2) CH$_2$—CH$_2$  3) H$_2$O
       \\O/

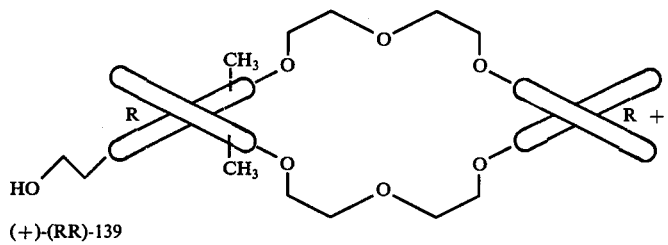

(+)-(RR)-139

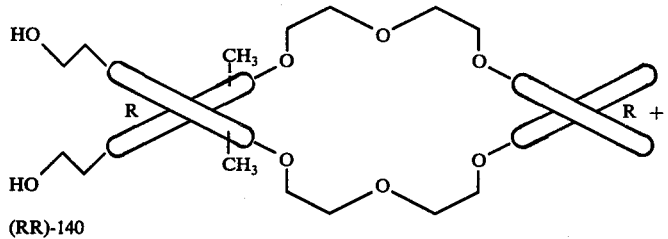

(RR)-140

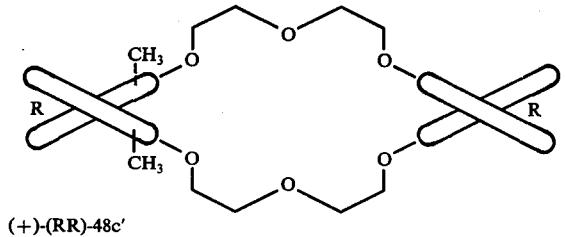

(+)-(RR)-48c′

Into a dry, three-necked flask, fitted with a jacketed and refrigerated addition funnel was placed a solution of 6.92 g. (7.95 mmole) of optically pure (+)-(RR)-135 (from Procedure 10) in dry 1,2-dimethoxyethane and a trace of triphenylmethane indicator. The solution was cooled to -75°, and with constant stirring under dry nitrogen, 8.05 ml. (17.7 mmole) of butyllithium (2.2M in hexane) was added with a dry hypodermic syringe through a rubber septum. The solution turned pink due to formation of the colored triphenylmethane anion. Ethylene oxide gas was dried carefully by passing it through a calcium sulfate tower (12 by 2 inch internal diameter), and condensed in the addition funnel (1.5 ml. or 30 mmole) into 6.5 ml. of dry 1,2-dimethoxyethane. After the initial reaction mixture had stirred for 2 hours at −75°, the ethylene oxide solution was added dropwise (15 minutes) under nitrogen and with stirring. The reaction mixture then was allowed to warm slowly to 25° over a period of 2 hours, during which the pink color disappeared. The mixture was stirred for 30 minutes at 25°, and 200 ml. of cold water was added. The mixture was shaken with dichloromethane, and the organic layer was dried and evaporated to give 6.6 g. of a white solid. This material was chromatographed on 300 g. of neutral alumina and eluted successively with 1 liter of dichloromethane to give 2.00 (34%) of fully protonated cycle ((+)-(RR)-48c, see Procedure 7), with 1.5 liters of 2% methanol in dichloromethane to give 3.74 g. (60%) of optically pure monoethoxylated cycle (+)-(RR)-139 [[α]$_{578}^{25}$ + 152° (C 1, CHCl$_3$)], and with 750 ml. of 3% methanol in dichloromethane to give 0.40 g. (6%) of diethoxylated cycle (RR)-140. The monoethoxylated cycle was submitted to dry column chromatography on neutral alumina with 25% methanol in dichloromethane (by volume) as solvent. The pure (+)-(RR)-139 was isolated as a white glass (dried at 90° at 0.01 mm.), 3.50 g. (56%), mass spectrum (76 eV) gave a molecular ion at m/e = 784, [α]$_{578}^{25}$ + 164° (C 1.7, CH$_2$Cl$_2$). The compound's complex pmr spectrum gave an A$_2$B$_2$ pattern at δ2.80 with a coupling constant J$_{AB}$ = 6Hz corresponding to the group, ArCH$_2$CH$_2$OH.

Anal. Calcd for C$_{52}$H$_{48}$O$_7$: C, 79.59; H, 6.12. Found: C, 79.29; H, 6.15.

The diethoxylated compound (RR)-140 was not characterized.

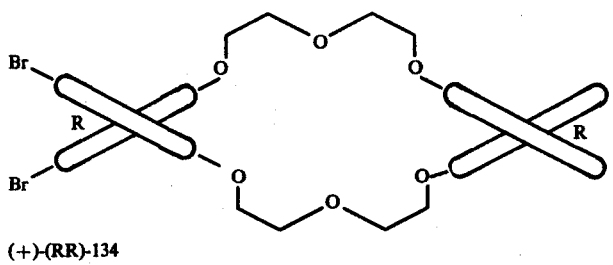

(+)-(RR)-134

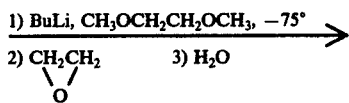

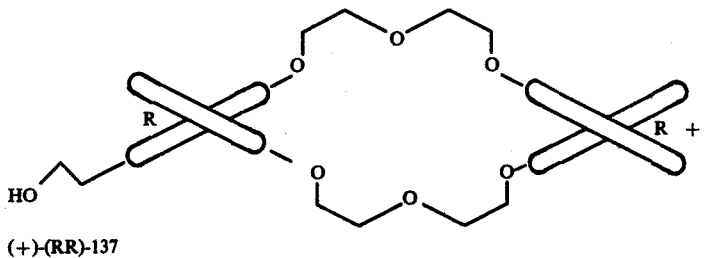

(+)-(RR)-137

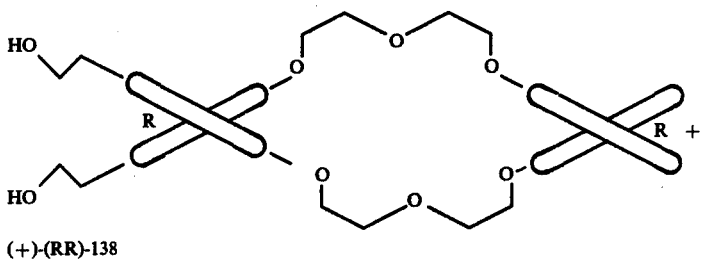

(+)-(RR)-138

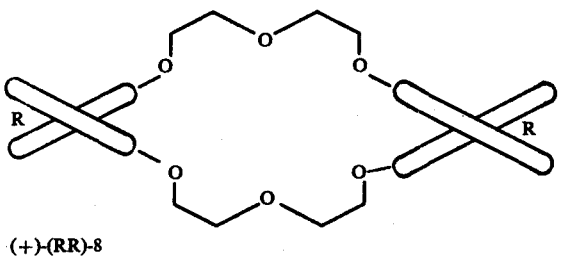

(+)-(RR)-8

Optically pure dibromocycle (+)-(RR)-134 from Procedure 10 was converted to optically pure (+)-RR-137 and (+)-(RR)-138 by the same procedure. Monoethoxylated cycle (+)-(RR)-137 was obtained as a white foam in 55% yield, $[\alpha]_{578}^{25} + 165°$ (C 1.13, $CH_2Cl_2$), whose mass spectrum (70 eV) gave molecular ion at m/e = 756.

Anal. Calcd. for $C_{50}H_{44}O_7$: C, 79.37; H, 5.82. Found: C, 78.90; H, 5.80.

Diethoxylated cycle (+)-(RR)-138 was obtained as a white foam in 10% yield, $[\alpha]_{578}^{25} + 162°$ (C 0.7, $CH_2Cl_2$), whose mass spectrum (70 eV) gave a molecular ion at m/e = 800.

Anal. Calcd. for $C_{52}H_{48}O_8$: C, 78.00; H, 6.00. Found: C, 77.69; H, 6.12.

Along with the two hydroxyethylated cycles was recovered 30% of optically pure and unwanted protonated cycle, (+)-(RR)-8, $[\alpha]_{578}^{25} + 227°$ (C 1, $CH_2Cl_2$) (see Procedure 6).

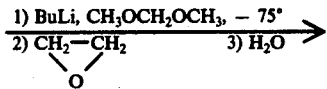

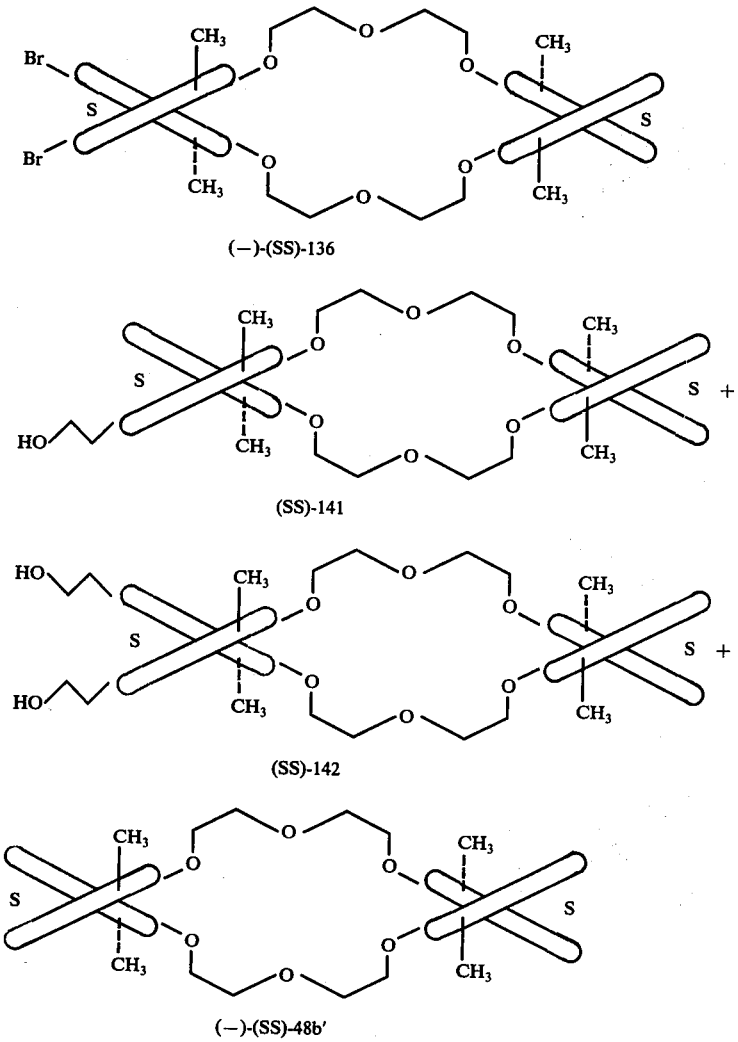

(−)-(SS)-136

(SS)-141

(SS)-142

(−)-(SS)-48b′

The same procedure was used to convert optically pure dibromotetramethylcycle (−)-(SS)-136 (from Procedure 10) into a mixture of (SS)-141 and (SS)-142 in a 30% yield which was separated by chromatography from tetramethylcycle (−)-(SS)-48b′ (60%), $[\alpha]_{578}^{25}$ −134° (C 1, CHCl$_3$).

Anal. Calcd. for $C_{52}H_{48}O_6$: C, 81.23; H, 6.28. Found: C, 81.38; H, 6.02.

The mixture of mono- and diethoxylated compounds, (SS)-141 and (SS)-142 were attached to resin directly (see Procedure 14).

Procedure 13

This procedure describes the chloromethylation of Amberlite XAD-2 obtained from Rohm and Haas Co.

The styrene-divinylbenzene copolymer, Amberlite XAD-2 [porosity (volume %) 42, surface area 330 m²/g, average pore diameter 90 A.], ground and sieved through a 150 mesh sieve, 103.4 g. (0.10 mole), was placed in a clean dry 1 liter flask followed by 150 ml. of ethylene dichloride. The slurry was then stirred at 25° for 30 minutes, after which 26.82 g. (0.30 mole) of chloromethyl methyl ether was added over a period of 15 minutes with constant stirring. Then 7.49 g. (0.05 mole) of solid aluminum chloride was added. The slurry was then stirred at 25°–30° for 4 hours and quenched with 300 ml. of methanol while maintaining the temperature at 25°–30° with an ice-water bath. After stirring for 15 minutes, the solvents were siphoned off using a suction flask (to which a gas dispersion tube was attached) connected to a vacuum pump, and the beads were allowed to settle to the bottom of the flask. This sequence was repeated a total of 4 times. The beads were then drained free of interstitial liquid, transferred to a pyrex flask and dried in a vacuum oven for 20 hours at 90° C. The final material weighed 109.6 g.

Elemental analysis of the final material gave the following: C, 86.58; H, 7.98; Cl, 3.97, or 1.12 milliequivalent of chlorine per gram of material. The figures for the starting resin were: C, 91.77; H, 8.07. Assuming that the equivalent weight of the polymer was 130, the theoretically calculated values for the non-chloromethylated resin were found to be: C, 91.77; H, 7.69. This material is referred to as 143.

The surface equivalent weight, or the equivalent weight of polymer necessary for one mole of surface rings, is 929 if we assume that the resin, XAD-2, has 14% of the rings present at the interface. The equivalent weight of the chloromethylated material will, therefore, be 976.5. The calculated theoretical chlorine content for 100% chloromethylation of the aromatic rings lying on the internal surface is, therefore, 3.63%. The chlorine content found (3.97%) experimentally is equivalent to chloromethylation of 15% of the aromatic rings, or an equivalent weight of 894 for the chloromethylated resin, or 845.7 for the non-chloromethylated resin.

Procedure 14

This procedure describes the attachment of hydroxyethylated cycles to resin 143.

saturated brine, and then dried over magnesium sulfate. Filtration and evaporation of the filtrate left a solid material, which was washed with pentane to remove the mineral oil and then redissolved in dichloromethane, evaporation of which left 1.8 g. of unreacted (+)-(RR)-137. This was chromatographed on 300 g. of alumina and eluted successively with 25% pentane-dichloromethane (1 liter), pure dichloromethane (1 li-

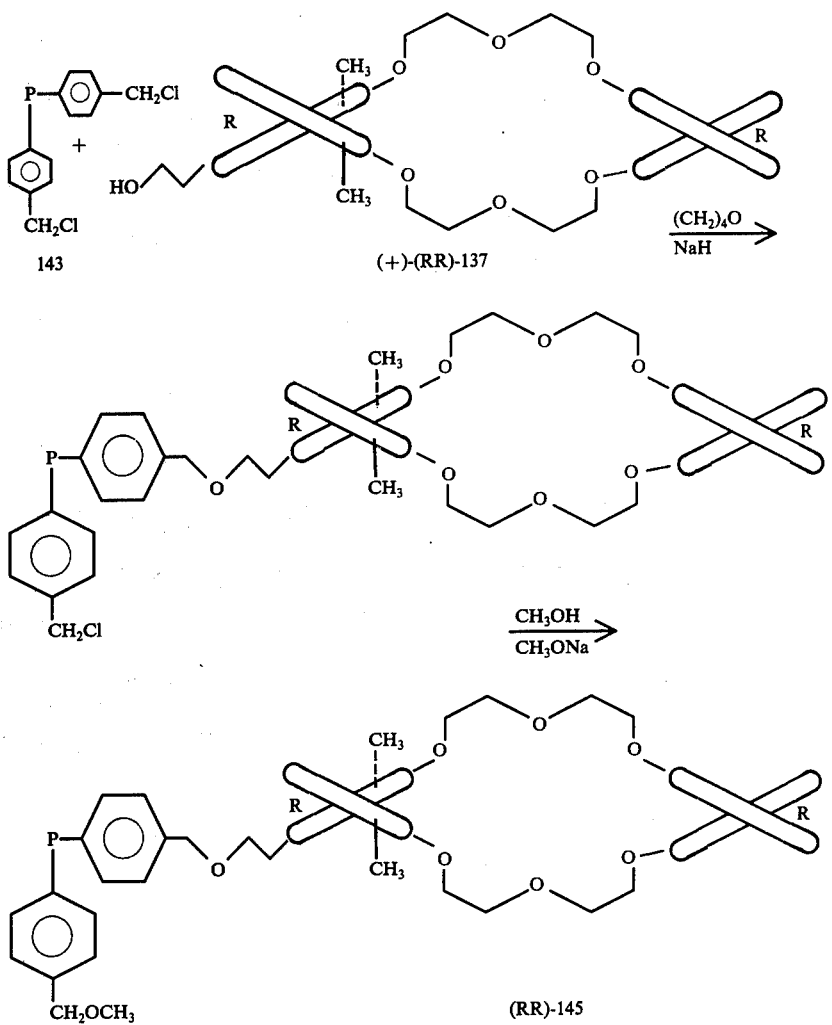

The procedure is illustrated with the synthesis of optically pure (RR)-145 from 143 (from Procedure 13) and optically pure (+)-(RR)-137 (from Procedure 12). To 2.53 g. (3.35 mmole) or (+)-(RR)-137 in 300 ml. of tetrahydrofuran was added 2.5 g. of NaH (50% dispersion in mineral oil), and the solution was heated at reflux for 30 minutes under nitrogen after which 29.0 g. of dry chloromethylated styrene-divinylbenzene resin was added under nitrogen. Refluxing was continued for 7 days. The reaction mixture was then cooled, filtered and the solids were washed successively with methanol (exothermic), water (with a trace of HCl), dichloromethane and methanol, and then dried at 90° in a vacuum oven (0.1 mm Hg) for 12 hours to give 30.3 g. of cycle grafted to resin, which gave on analysis, 3.71% chlorine.

The washings and the filtrate were combined and the organic layer was separated, washed with water and ter), and 2% methanol in dichloromethane to give 1.30 g. of purified (+)-(RR)-137. The difference between the amount of (+)-(RR)-137 used and the crude amount recovered was used to calculate the amount of cycle bound to resin. The value of 0.073 mmole of cycle per gram obtained is consistent with the loss in chlorine content of the resin during reaction.

To 30.3 g. of the grafted resin mixed with 250 ml. of absolute methanol was added 15.4 g. (0.29 mole) of sodium methoxide, and the solution was refluxed for 15 hours, cooled, acidified with hydrochloric acid to pH 5 (very exothermic), filtered, washed thoroughly with water and methanol, and dried at 90° in vacuo (0.11 mm Hg) for 12 hours. The final useful (RR)-145 weighed 30.3 g., and gave 0.65% chlorine upon analysis. Thus the final material contained 0.073 mmole of cycle per gram, 0.18 milliequivalent of chlorine per gram and 0.87 milliequivalent of methoxyl groups per gram.

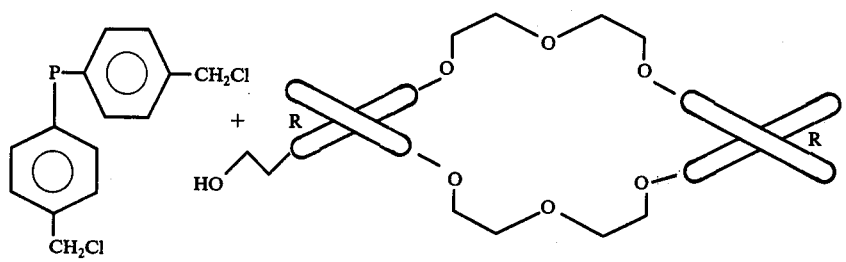

143            (+)-(RR)-137

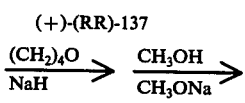

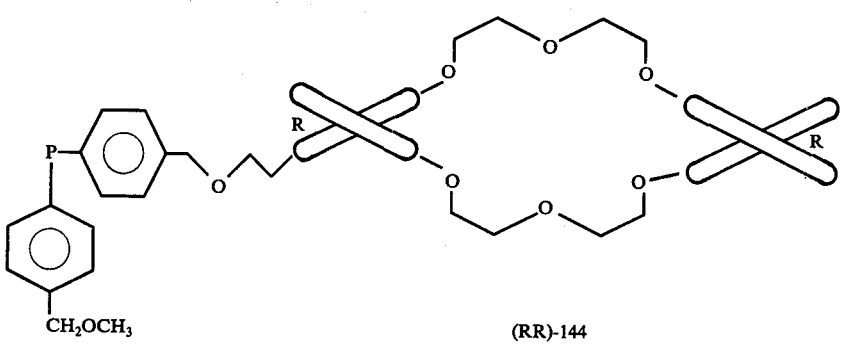

(RR)-144

Application of the same procedure to optically pure (+)-(RR)-137 (from Procedure 12) and 143 (from Procedure 13) gave optically pure (RR)-144. The initial polymer-bound product before methoxylation gave 3.80% chlorine, and after methoxylation gave 0.60 % Cl. The grafted polymer produced ((RR)-144) contained about 0.048 mmole of cycle per gram, 0.17 milliequivalent of chlorine per gram, and 0.90 milliequivalent of methoxyl groups per gram.

146. The final polymer-bound product, (SS)-146 contained about 0.041 mmole of cycle per gram, 0.20 milliequivalent of chlorine per gram, and 0.804 milliequivlent of methoxyl groups per gram.

The cycle-bound resins did not swell appreciably when mixed with organic solvents or water.

Technique of Chromatographic Optical Resolution of Amino Acids and Their Derivatives The host-bound resin was ground in a Wiley Laboratory Mill, Standard Model No. 3, and sieved to give material of 250–325 mesh used in the larger and 325–400 mesh in the smaller columns. This resin was suspended

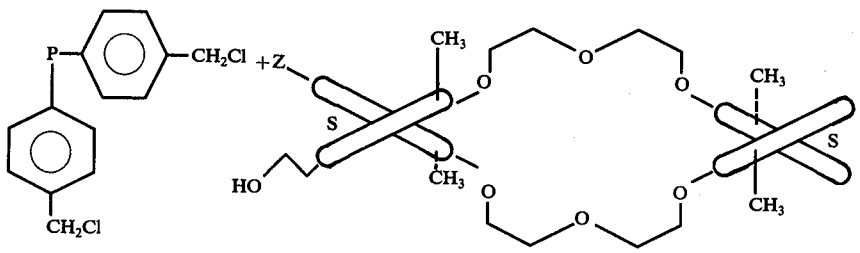

mixture of (SS)-141 (Z=H) and
(SS)-142 (Z=CH₂CH₂OH)

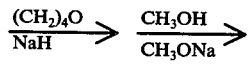

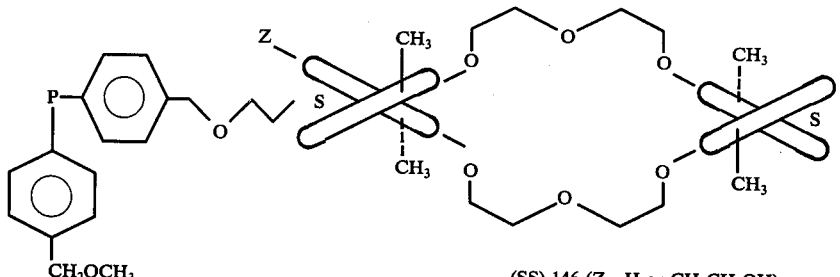

(SS)-146 (Z=H or CH₂CH₂OH)

Application of the same procedure to 143 (from Procedure 13) and a mixture of optically pure (SS)-141 and (SS)-142 (from Procedure 12) gave optically pure (SS)- in acetonitrile-chloroform (1:1 by volume) and transferred into a "cartridge" stainless steel column, of twice the length but the same bore as the final chromatograph column. The cartridge column was connected to the stainless steel precision bore chromatograph column containing the same solvent mixture. The slurry in the cartridge was pumped at 3 ml. per minute (800–900 psi) into the chromatograph column fitted with a porous plug at the outlet. A Milton Roy Mini-Pump with a maximum capacity of 160 ml. per minute was used in both the loading and operation of the columns. The chromatograph columns were jacketed and insulated for constant temperature control. Pure, dry and degassed solvents were used in loading, washing, storing or running the chromatograph columns. The resin particles were rapidly filtered out of the slurry onto the porous plug at the bottom of the chromatograph column, leaving a stable bed. After loading, the columns were conditioned by washing with one liter of methanol, one liter of chloroform and one liter of the desired mobile phase.

The columns were fitted for introduction of sample with injection loops removed from a Waters Associate Chromatograph Model 202. The bottoms of the columns led to conductivity cells of 0.1 ml. capacity made from two brass plates held apart by a Teflon gasket, which had a cell constant of ~ 0.017 cm$^{-1}$. The cells were electrically attached to a Phillips PR 9501 direct reading conductivity bridge attached to a recorder. The relative conductivity ($\mu$mho) of the cells were found to be proportional to the concentration of alkylammonium perchlorate or hexafluorophosphate salt in 10% acetonitrile in chloroform. The dead volume of each column was determined by injecting the non-retained compounds, methanol, benzene, hexane and pentane as samples onto the columns, and determining their retention volumes. The larger column was 60 by 0.75 (i.d.) cm. in dimension. With fittings and packed with resin it was found to possess a non-occupied volume of 23.76 ± 0.04 ml. When corrected for the volumes of the connecting tubes and injection loop, the dead volume (that not occupied by resin) of the column itself was found to be 18.36 ± 0.04 ml. The smaller columns were 60 by 0.40 (i.d.) cm. With fittings and packed with resin they were found to possess a non-occupied volume of 9.50 ± 0.50 ml., which when corrected for the volumes of tubings and injection loop, was 7.50 ± 0.50 ml. At the end of runs, the columns were washed with methanol and then with the solvent used for the next run. The columns were stored under methanol, and did not appear to deteriorate with time or use.

The optical resolutions of racemates is exemplified with three packed columns, referred to as Columns A, B and C. Column A was of the larger dimension (see above), and contained 9.5 g. of (RR)-145 as resin-bound host. Column B was of the smaller dimension (see above) and contained 4.0 g. of (RR)-145 as resin-bound host. Column C was of the smaller dimension and contained 4.0 g of (RR)-144 as resin-bound host.

The columns were run at constant temperature by passing constant temperature liquid through their jacekts. They were also run at constant flow rates between 0.27 and 2.0 ml./min. with pressure drops between 350 to 900 pounds per square inch. Between 0.013 and 84 mg. per run of racemic alkylammonium perchlorate or hexafluorophosphate salt dissolved in a minimum amount of solvent was injected into the loop at the top of the column. The appearance of the enantiomers in the column eluate was detected by the conductivity cell. Plots of Relative Conductance ($\mu$mho) against Volume of Eluate (ml.) provided a means of determining how well the enantiomers of a racemate were separated by the column (see next section). The mobile phases were chloroform or dichloromethane containing small amounts of acetonitrile or ethyl acetate (5 to 25% by volume) to act as salt-solubilizers and carriers.

Results of Optical Resolution of Racemic Alkylammonium Salts By Chromatography

The effectiveness of optical resolution of the racemates is measured by chromatographic parameters [Snyder and Kirkland, "Introduction to Modern Liquid Chromatography", Wiley N.Y., 1974]. These parameters are described briefly here.

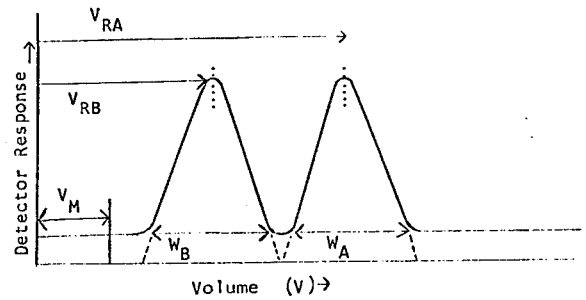

Graph 1 — Chromatogram plot of Detector Response against eluate Volume (V) in which $V_M$ is defined as dead volume, $V_{RA}$ and $V_{RB}$ as retention volumes of less and more retained enantiomers respectively, and $W_A$ and $W_B$ as bandwidths of less and more retained enantiomers, respectively.

Chromatographic runs are characterized by parameters measured from plots of Detector Response against Column Eluate Volume.

Graph 1 is an idealized plot of a chromatographic run in which Volume (V) definitions are highlighted. The retention volume, $V_R$, of a sample component represents the volume of the mobile phase required to elute the same. The elution volume of a completely non-retained component, $V_M$, is the dead volume, the volume of the chromatograph column occupied by the mobile phase and not occupied by the solid phase.

Enantiomer A is defined as that enantiomer less firmly complexed by the host on a solid support, and B as that enantiomer more firmly complexed. Thus $V_{RA}$ is defined as the retention volume of the enantiomer that appears last in the column eluate and $V_{RB}$ is that of the enantiomer that appears first. A measure of the relative binding ability of a column for the two enantiomers is provided by the enantiomer separation factor, defined as $\mu$ in equation (1). By definition, $\mu$ is always equal to or greater than unity. The higher its value, the greater the free energy difference of binding of each enantiomer by the column, and the greater the possibility of complete separation of enantiomers in a chromatogram.

$$\alpha = (V_{RA} - V_M)/(V_{RB} - V_M) \tag{1}$$

The efficiency of separation of the two enantiomers is measured by the parameter, $R_S$, called the resolution factor, defined by equation (2), in which $W_A$ is defined as the bandwidth of enantiomer A, and $W_B$ as that of enantiomer B. The higher the value of $R_S$, the more complete is the optical resolution. Values of $R_S$ of 0.8 or more provide complete separation of all of each enantiomer from the other, while values from 0.2 to 0.8 provide complete separation of part of each enantiomer from the other provided eluate fractions are properly cut. In plots of detector response vs. eluate volume, if the base line is reached in between fractions, complete separation is accomplished. If a minimum between fractions is observed, usually judicious cutting of fractions will provide some of each component in an optically pure state.

$$R_S = 2[(V_{RA} - V_{RB})/W_B + W_A)]$$

The ratio of molar amounts of host bound to the solid support of a column to the molar amounts of guest in the mobile phase ([H]/[G]) is a column parameter that provides a rough molecular measure of how much host is required to optically resolve a given amount of guest. It is important to know how much solid support is needed for a chromatogram to effect separation of a given amount of racemate (guest).

Table I reports the results of chromatographic runs conducted with ten different aminoacid perchlorate salts. Runs 1–33 involved Columns A and B which were packed with (RR)-145 (see Procedure 14), and runs 34–37 involved Column C packed with 4.0 g. of (RR)-144 (see Procedure 14). The peaks of plots of relative conductance (Detector Response) vs. Volume of Column Eluate gave peaks Gaussian in shape, and little tailing was observed.

Table 1.

Optical Resolution of R—$\overset{*}{C}H(\overset{+}{NH_3})$—$CO_2H$ $ClO_4^-$(Guest) by Solid-Liquid Chromatography[a] on Columns A[b,c], B[c,k] and C[k,m]

| Run no. | Column used | Guest Structure of R | Wt. (mg) | [H][d] / [G] | Mobile phase[e] Solv. | Carrier Kind | % [f] | T °C | Separation factor $\alpha^g$ | Kind | Resol. Factor $R_s^h$ |
|---|---|---|---|---|---|---|---|---|---|---|---|
| 1 | A | $C_6H_5$ | 0.013 | 14,000 | $CHCl_3$ | MeCN | 10 | 0 | 5.5 | Base 1. | 1.99 |
| 2 | A | $C_6H_5$ | 0.13 | 1,400 | $CHCl_3$ | MeCN | 10 | 0 | 8.9 | Base 1. | 2.72 |
| 3 | A | $C_6H_5$ | 0.32 | 550 | $CHCl_3$ | MeCN | 10 | 0 | 11.0 | Base 1. | 2.89 |
| 4 | A | $C_6H_5$ | 0.60 | 290 | $CHCl_3$ | MeCN | 10 | 0 | 11.6 | Base 1. | 2.86 |
| 5 | A | $C_6H_5$ | 1.0 | 170 | $CHCl_3$ | MeCN | 10 | 0 | 10.7 | Base 1. | 2.35 |
| 6 | A | $C_6H_5$ | 1.9 | 91 | $CHCl_3$ | MeCN | 10 | 0 | 12.2 | Base 1. | 1.76 |
| 7 | A | $C_6H_5$ | 3.1 | 57 | $CHCl_3$ | MeCN | 10 | 0 | 10.6 | Base 1. | 1.21 |
| 8 | A | $C_6H_5$ | 5.0 | 35 | $CHCl_3$ | MeCN | 10 | 0 | 14.6 | Base 1. | 1.13 |
| 9 | A | $C_6H_5$ | 10.1 | 17 | $CHCl_3$ | MeCN | 10 | 0 | 24.3 | Base 1. | 0.74 |
| 10 | A | $C_6H_5$ | 15.2 | 11 | $CHCl_3$ | MeCN | 10 | 0 | 12.2 | Base 1. | 0.76 |
| 11 | A | $C_6H_5$ | 20.5 | 8 | $CHCl_3$ | MeCN | 10 | 0 | 10.0 | Minim. | 0.54 |
| 12 | A | $C_6H_5$ | 84 | 2 | $CHCl_3$ | MeCN | 10 | 0 | 10.7 | Minim. | 0.20 |
| 13 | A | $C_6H_5$ | 5.08 | 34 | $CHCl_3$ | EtOAc | 5 | 25 | 4.5 | Base 1. | 1.35 |
| 14 | A | $C_6H_5$ | 5.04 | 35 | $CHCl_3$ | EtOAc | 5 | 0 | 10.9 | Base 1. | 1.92 |
| 15 | A | $C_6H_5$ | 16.1 | 11 | $CHCl_3$ | EtOAc | 10 | 0 | 7.4 | Base 1. | 1.23 |
| 16 | A | $C_6H_5$ | 16.0 | 11 | $CHCl_3$ | EtOAc | 15 | 0 | 4.7 | Minim. | 0.61 |
| 17 | A | $C_6H_5$ | 5.1 | 34 | $CHCl_3$ | EtOAc | 25 | 0 | 4.3 | Base 1. | 0.85 |
| 18 | A | $C_6H_5$ | 15.7 | 11 | $CH_2Cl_2$ | MeCN | 5 | 0 | 5.3 | Base 1. | 1.22 |
| 19 | A | $C_6H_5$ | 14.5 | 12 | $CH_2Cl_2$ | MeCN | 17 | 0 | 3.4 | Minim. | 0.39 |
| 20 | A | $C_6H_5$ | 14.7 | 12 | $Et_2O$ | MeCN | 10 | 0 | 1.0 | None | 0.00 |
| 21 | A | p-$HOC_6H_4$ | 6.6 | 28 | $CHCl_3$ | MeCN | 10 | 0 | 6.1 | Base 1. | 2.31 |
| 22 | A | $C_6H_5CH_2$ | 4.6 | 40 | $CHCl_3$ | MeCN | 4 | 0 | 2.3 | Base 1. | 0.97 |
| 23 | A | p-$HOC_6H_4CH_2$ | 5.8 | 36 | $CHCl_3$ | MeCN | 10 | 0 | 1.9 | Minim. | 0.42 |
| 24 | A | $C_8H_6NCH$[j] | 2.0 | 104 | $CHCl_3$ | MeCN | 20 | 0 | 6.1 | Base 1. | 1.61 |
| 25 | A | $(CH_3)_2CH$ | 1.6 | 97 | $CHCl_3$ | MeCN | 10 | 0 | 2.3 | Minim. | 0.45 |
| 26 | A | $C_2H_5(CH_3)CH$ | 2.3 | 69 | $CHCl_3$ | MeCN | 5 | 0 | 1.9 | Minim. | 0.24 |
| 27 | A | $(CH_3)_3C$ | 2.0 | 79 | $CHCl_3$ | MeCN | 5 | 0 | 1.9 | Minim. | 0.37 |
| 28 | A | $CH_3$ | 1.6 | 82 | $CHCl_3$ | MeCN | 4 | 0 | 1.5 | Minim. | 0.21 |
| 29 | A | $CH_3SCH_2CH_2$ | 6.6 | 26 | $CHCl_3$ | MeCN | 4 | 0 | 1.4 | Minim. | 0.25 |
| 30[k] | B | $C_6H_5$ | 1.7 | 43 | $CHCl_3$ | MeCN | 10 | 25 | 4.1 | Base 1. | 0.89 |
| 31[k] | B | p-$HOC_6H_4$ | 2.4 | 32 | $CHCl_3$ | MeCN | 10 | 25 | 4.2 | Base 1. | 1.55 |
| 32[k] | B | $C_6H_5CH_2$ | 1.0 | 75 | $CHCl_3$ | MeCN | 10 | 25 | 1.2 | Minim. | 0.25[l] |
| 33[k,m] | B | $(CH_3)_3C$ | 1.4 | 47 | $CHCl_3$ | MeCN | 5 | 25 | 1.4 | Minim. | 0.52 |
| 34[k,m] | C | $C_6H_5$ | 2.0 | 23 | $CHCl_3$ | MeCN | 2.5 | 0 | 2.4 | Minim. | 0.35 |
| 35[k,m] | C | p-$HOC_6H_4$ | 1.7 | 30 | $CHCl_3$ | MeCN | 10 | 0 | 1.8 | Minim. | 0.23 |
| 36[k,m] | C | p-$HOC_6H_4CH_2$ | 1.1 | 48 | $CHCl_3$ | MeCN | 5 | 0 | 1.6 | Minim. | 0.21 |
| 37[k,m] | C | $C_2H_5(CH_3)CH$ | 1.0 | 44 | $CHCl_3$ | MeCN | 5 | 0 | 2.0 | Minim. | 0.21 |

[a]Flow rate 0.36 to 2.0 ml./min. pressure, 650–900 psi.
[b]60 by 0.75 cm (i.d) stainless steal jacketed (insulated) column packed with 250–325 mesh resin, dead volume 18.4 ml.
[c]0.073 mmole of host/g, (RR)-145 (average host site ~14,000 molecular weight).
[d]Ratio moles of host to guest.
[e]Reagent grade solvents, $CHCl_3$ contained 0.75% EtOH.
[f]By volume.
[g]$\alpha$=(retention volume of less mobile component minus total dead volume)/(retention volume of more mobile component minus total dead volume).
[h]$R_s$=2(retention volume of less mobile component minus that of more mobile component)/(sum of bandwidths of the two peaks).
[i]% of each enantiomer put on column complexed to stationary phase at equilibrium.
[j]$\beta$-methylenylindole.
[k]60 by 0.40 cm (i.d.) stainless steel jacketed (insulated) column packed with 4.00 g. of 325–400 mesh resin, dead volume 7.5 ml.
[l]Peaks overlapped too much to allow good determination.
[m](RR)-144 0.048 mmole/g (average host site ~21,000 molecular weight) was attached to resin of this column.
"Base 1." means base line.

The configurational identities and optical purities of the faster (less complexed) and slower (more complexed) moving enantionmers were identified by isolation and characterization of the pure antipodes in runs 11, 21, 22 and 28, and by determination of the signs of rotation of eluate fractions in runs 23–27, 29 and 34–37.

In the many runs with base-line separations of enantiomers, the areas under the peaks for the two enantiomers were within experimental error of being equal. Separation factors ($\alpha$) ranged from a high of 24 (run 9) to a low of 1.2 (run 32). Graphs 2 and 3 are plots that represent of the extremes in $R_s$ values (runs 3 and 28, respectively).

The larger column with (RR)-145 as host and phenylglycine as guest was particularly well characterized (runs 1-20). Chloroform as solvent and 10% (v) acetonitile as carrier generally gave the best results, although chloroform-ethyl acetate (5%, v) gave comparable results with equal amounts of guest (compare runs 8 and 14). Good hydrogen bond acceptors such as methanol, diethyl ether (run 20) or tetrahydrofuran gave only one peak. Higher chiral recognition (higher $\alpha$'s) were observed at 0° than at 25°. For example, both $\alpha$ and $R_s$ are 1 mg. of salt ([H]/[G]=17). The maximum $R_s$ value (2.89) was found in run 3 ($\alpha=11$) in which 0.32 mg. of salt ([H]/[G]=550) was used. The column's remarkable feature is that the amount of salt could be varied by a factor of about 6,500, and good optical resolution was effected, even when the column was badly overloaded (~run 12). Thus the same column serves both preparative and analytical purposes.

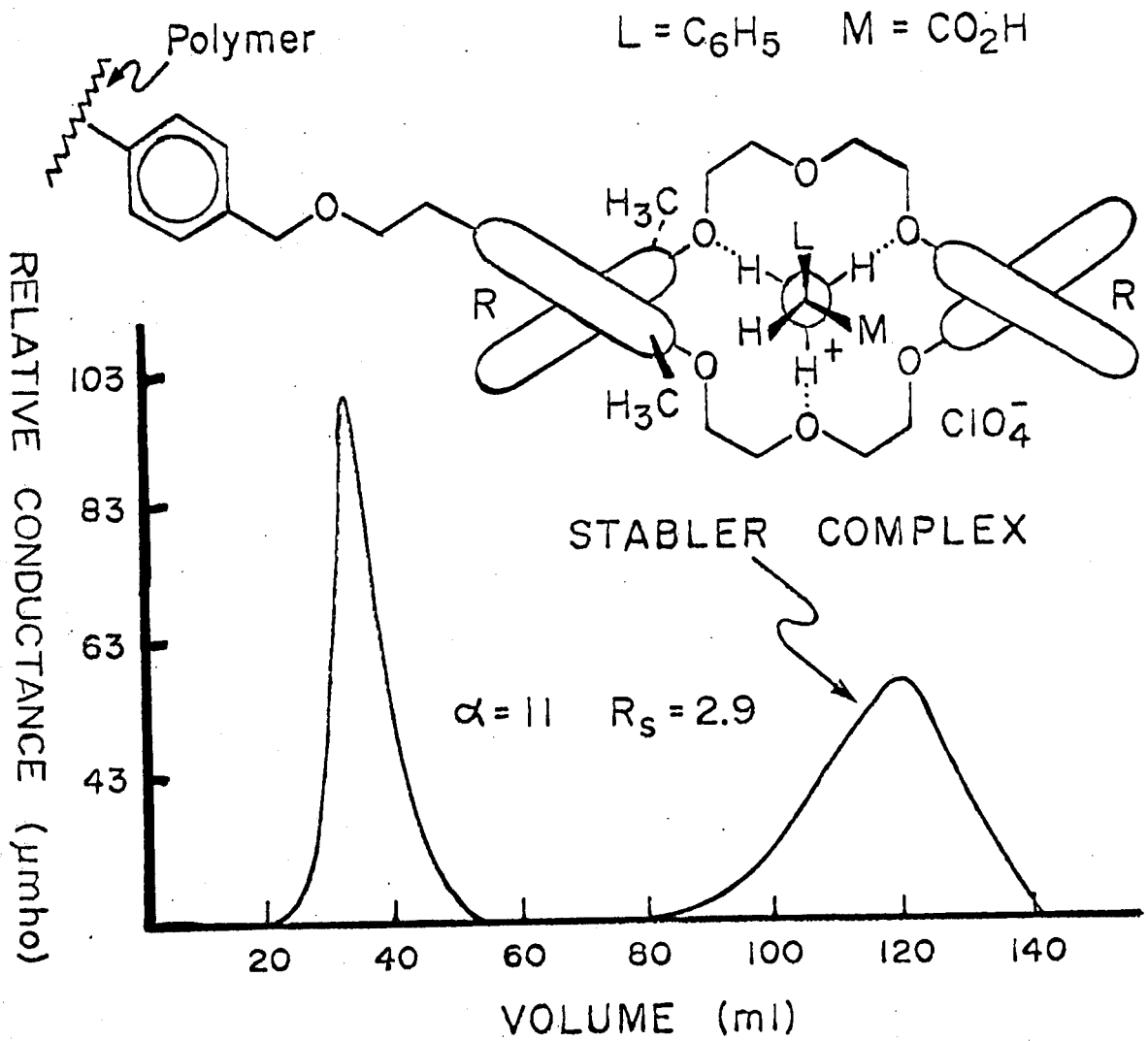

substantially higher in run 14 than in run 13. In runs 1-12, the amount of salt put on the column was varied between 0.013 and 84 mg. The maximum $\alpha$ value (24) was observed in run 9 ($R_s = 0.74$) which involved 10.1

Graph 2 — Plot of Relative Conductance against column eluate Volume for chromatographic run 3 of Table 1 with (RR)-145 as immobile phase and phenylglycine salt in the mobile phase.

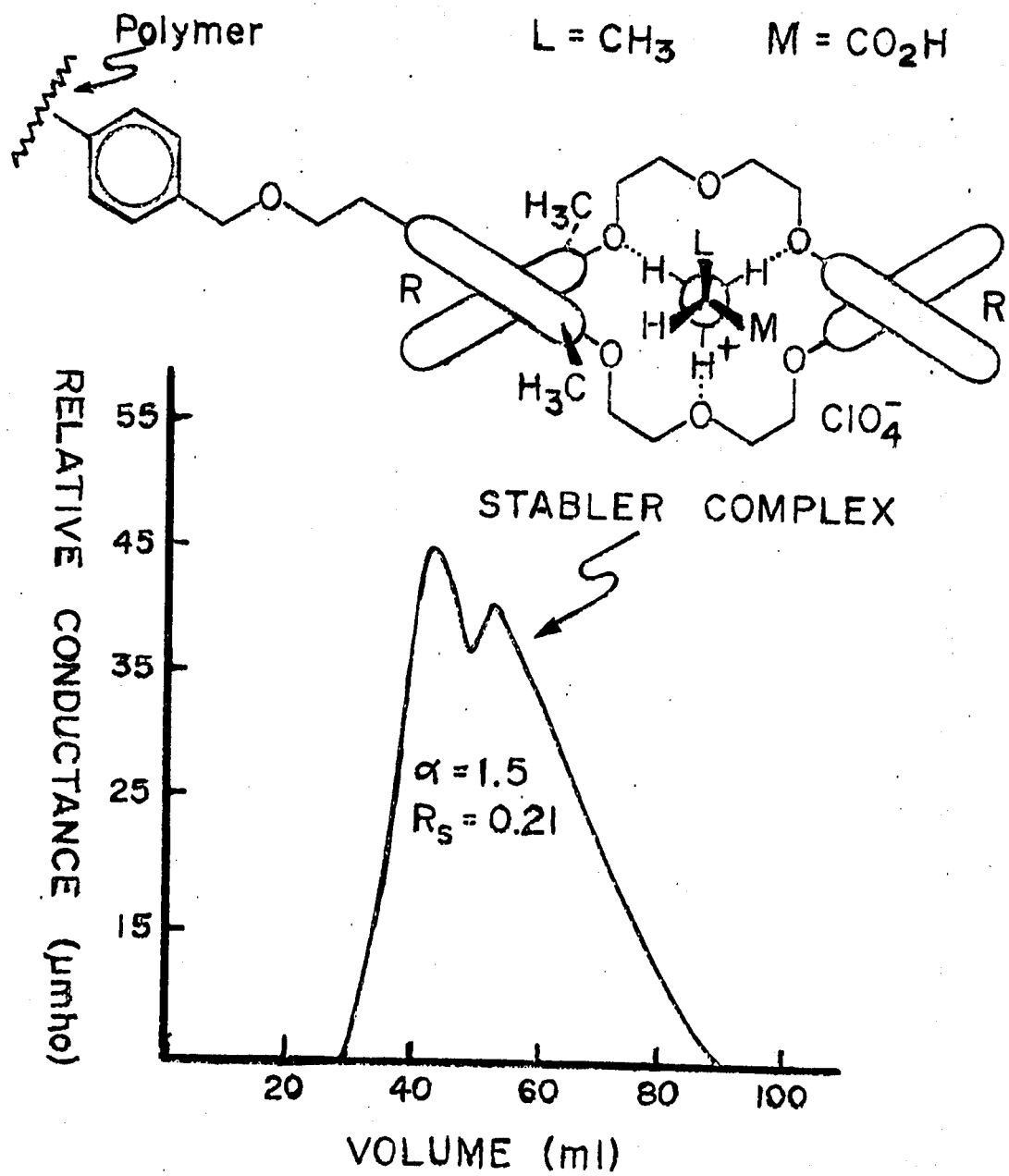

Graph 3 — Plot of Relative Conductance against column eluate Volume for chromatographic run 28 of Table 1 with (RR)-145 as immobile phase and alanine salt in the mobile phase.

The α values for the different amino acid salts decreased in the order phenylglycine (14.6, run 8) > tryptophane (6.1, run 23) ~p-hydroxyglycine (6.1, run 21) > phenylalanine (2.3, run 22) ~-valine (2.3, run 25) > tyrosine (1.9, run 23) ~isoleucine (1.9, run 26) ~tert-leucine (1.9, run 27) > alaine (1.5, run 28) > methionine (1.4, run 29). Base-line resolutions were observed for all the aryl amino acids except tyrosine, and even with the amino acid with the poorest separation factor (methionine) a substantial amount of each enantiomer could be obtained optically pure by a proper cutting of fractions.

With all of the amino acids except phenylalanine (runs 22 and 32) the (R)-enantiomer was more closely bound, which also was observed with the esters (see below). Thus hydrogen bonding of the carboxyl group to the host does not play a dominant role in determining the relative stabilities of the diastereomeric complexes. The p-phenyl substituents appear to be more important in determining the relative diastereomeric stabilities (compare phenylglycine and p-hydroxyphenylglycine in runs 8 and 21, and phenylalanine and tyrosine in runs 22 and 23). Structure 147 is visualized as the more stable diastereomer for all complexes except that of phenylalanine. The same explanation is offered for the unique behavior of phenylalanine as is suggested for that of its methyl ester (see below).

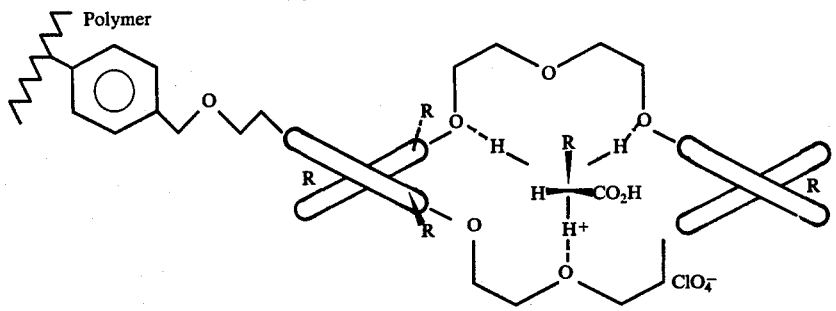

147

The thinner column containing 4.00 g. of (RR)-145 gave with four different amino acids at 25° results qualitatively similar to those obtained at 0° with 9.5 g. of (RR0-145 (runs 30-33). The lower α values obtained are attributed to the higher temperature used in the thinner column. In runs 34-37 at 0°, (RR)-144 was used as packing, and the chiral recognition decreased markedly. The two methyl groups in (RR)-145 extend the chiral barrier and provide a more shaped cavity than (RR)-144 in which the methyls are absent. The same effect was observed with the same host sites in solution in chloroform when the enantiomers of amino ester salts were differentially extracted from water [J. Amer. Chem. Soc., 96, 6762 (1974)]. Thus the effects of structural changes on chiral recognition in both host and guest at the interface and in solution are strikingly similar.

These columns and others like them show promise of being useful for both preparative and analytical purposes. The different amino acid salts have different retention volumes, which allows analysis for both the kind and optical purities of mixtures of amino acids and of their derivatives at acyl carbon. No primary ammonium salt has yet been put on the columns without some resolution occurring. No noticeable deterioration of the columns' effectiveness has been observed over a period of months.

Table II reports the results of chromatograms run on the hexafluorophosphate or perchlorate salts of the methyl esters of phenylglycine, p-chlorophenylglycine, p-carbomethoxyphenylglycine, p-hydroxyphenylglycine, phenylalanine, p-fluorophenylalanine and tyrosine. Between 0.5 and 25 mg. of guest salt was used per run. Plots of relative conductance vs. the volume of eluate gave Gaussian peaks with essentially no tailing for each enantiomer for all runs. The absence of tailing makes these supports much superior to those of most chromatograph columns. Good hydrogen bond acceptors such as $(CH_2)_4O$ and $CH_3OH$ as the mobile phase eluted both enantiomers with the solvent front. The resin volume did not change observably with solvent changes. Base-line separation of peaks was realized in all runs but 2, 5 and 6. Well-defined minima reaching from 35 to 90% of the way to the base line were observed in these runs. In all runs but 10-13 the configurational identities of the more and less firmly bound enantiomers were determined either by comparisons of their retention volumes with those of authentic enantiomers, or from the signs of rotations of eluate fractions. Optically pure enantiomers were isolated from runs 3, 4 and 12, and identified by the signs and magnitudes of their rotations. Runs 10-13 involved guest compounds which have not been resolved by conventional methods and whose configurations were previously unknown. These compounds were resolved preparatively on Column A and each enantiomer was obtained optically pure. Comparisons of the Circular Dichroism (CD) curves of the more and less bound enantiomers in these runs with those of the runs involving p-hydroxyphenyl and phenylglycine ester salts (configurations known) indicated the more bound isomers were of the (R)-configuration in runs 10-12. Similarly, p-fluorophenylalanine methyl ester perchlorate salt was resolved preparatively, and each enantiomer was obtained optically pure. Their configurations were determined by CD curve comparisons with those of the methyl ester salts of (L)-phenylalanine and (L)-tyrosine. For all runs, the separation factors (α) ranged from 1.7 to 26 and the resolution factors ($R_s$) from 0.25 to 4.5.

Table II

Optical Resolution of $R-\overset{\overset{+\quad -}{NH_3X}}{\underset{|}{CH}}-CO_2CH_3$ by Solid-Liquid Chromatography on (RR)-144 (Column C[a]) and (RR)-145 (Columns B[a] and A[b]).

| Run no. | Host Column | mmol | wt(g) | Guest R | X⁻ | [H][c] [G] | Mobile phase[d] | T °C | Sep. fact. α | $R_s$ | Config. bound G |
|---|---|---|---|---|---|---|---|---|---|---|---|
| 1 | C | 0.19 | 4.0 | C₆H₅ | PF₆⁻ | 11 | CHCl₃-5% MeCN | 0 | 4.1 | 0.48 | R |
| 2 | C | 0.19 | 4.0 | C₆H₅ | PF₆⁻ | 116 | CHCl₃-10% MeCN | 0 | 1.7 | 0.25 | R |
| 3 | B | 0.29 | 4.0 | C₆H₅ | PF₆⁻ | 36 | CHCl₃-5% MeCN | 25 | 4.3 | 0.77 | R |
| 4 | B | 0.29 | 4.0 | C₆H₅ | ClO₄⁻ | 38 | CHCl₃-10% MeCN | 25 | 4.3 | 1.02 | R |
| 5 | B | 0.29 | 4.0 | C₆H₅CH₂ | ClO₄⁻ | 31 | CHCl₃-5% MeCN | 25 | 3.2 | 0.58 | S |
| 6 | B | 0.29 | 4.0 | p-HOC₆H₄CH₂ | ClO₄⁻ | 31 | CHCl₃-10% MeCN | 25 | 2.2 | 0.24 | R |
| 7 | A | 0.69 | 9.5 | p-HOC₆H₄ | ClO₄⁻ | 50 | CHCl₃-10% MeCN | 0 | 26 | 3.0 | R |
| 8 | A | 0.69 | 9.5 | C₆H₅ | ClO₄⁻ | 48 | CHCl₃-10% MeCN | 0 | 18.5 | 4.5 | R |
| 9 | A | 0.69 | 9.5 | C₆H₅ | ClO₄⁻ | 86 | CHCl₃-5% MeCN | 0 | 18.2 | 4.5 | R |
| 10 | A | 0.69 | 9.5 | p-CH₃O₂CC₆H₄ | ClO₄⁻ | 50 | CHCL₃-10% MeCN | 0 | 12.6 | 2.3 | R |
| 11 | A | 0.69 | 9.5 | p-ClC₆H₄ | ClO₄⁻ | 47 | CHCl₃-10% MeCN | 0 | 8.5 | 2.2 | R |
| 12 | A | 0.69 | 9.5 | p-ClC₆H₄ | PF₆⁻ | 48 | CHCl₃-10% MeCn | 0 | 8.1 | 1.3 | R |
| 13 | A | 0.69 | 9.5 | p-FC₆H₄CH₂ | ClO₄⁻ | 50 | CHCl₃-10% MeCN | 0 | 8.5 | 2.7 | S |
| 14 | A | 0.69 | 9.5 | C₆H₅CH₂ | ClO₄⁻ | 50 | CHCl₃-10% MeCN | 0 | 6.4 | 1.9 | S |
| 15 | A | 0.69 | 9.5 | p-HOC₆H₅CH₂ | ClO₄⁻ | 47 | CHCl₃-10% MeCN | 0 | 4.7 | 1.7 | R |

[a]60 by 0.40 cm (i.d.) stainless steel jacketed (insulated) column packed with 4.00 g. of 325-400 mesh (RR)-144 or (RR)-145 dead volume 7.55 ml.
[b]60 by 0.75 cm. (i.d.) stainless steel jacketed (insulated) column packed with 9.6 g. of 250-325 mesh (RR)-145, dead volume 18.4 ml.
[c]Ratio of moles of host to guest.
[d]By volume.

The methyl esters of racemic p-chlorophenylglycine hydrochloride, m.p. 194°-197°, and racemic p-carbomethoxyphenylglycine hydrochloride, m.p. 200°-201° were prepared from the corresponding acids [Biochemistry, 5, 203 (1966)]. The optically pure methyl ester perchlorate salts after preparative resolution by chromatography on Column A gave: for the p-chloro derivative, m.p. 82.5° for the less retained enantiomer A, $\alpha]25/578 + 73.7°$ (C, 0.83, MeOH) and m.p. 82° for the more retained enantiomer B, $[\alpha]25/578 - 69.5°$ (C, 0.77, MeOH); for the p-carbomethoxy derivative, less retained enantiomer A, m.p. 53.5°, $[\alpha]25/578 + 75.9°$ (C 0.80, MeOH) and more retained enantiomer B, m.p. 53°, $[\alpha]25/578 - 76.0°$ (C 0.80, DMeOH). The methyl ester perchlorate salts of p-fluorophenylalanine gave: m.p. 79° for the less retained enantiomer A, $[\alpha]25/578 + 35.5°$ (C 0.80, MeOH) and m.p. 79.5° for the more retained enantiomer B, $[\alpha]25/578 - 33.8°$ (C 0.80, MeOH). The CD spectrum of all four phenylglycine and three phenylalanine methyl ester salts in MeOH (C 0.8 ± 0.1) gave Cotton effects at 215-220 nm ($\pi \rightarrow \pi^*$) whose sign was configuration dependent, and at 250-260 nm whose sign was configuration independent and negative. The ester salts of known configuration correlated as follows: (S)-phenylglycine, ~220 nm, $[\theta]$ = + 1260°; (R)-p-hydroxyphenylglycine, ~215 nm, $[\theta]$ = −950°; (S)-phenylalanine, ~220 nm, $[\theta]$ = + 800°; (S)-tyrosine, ~220 nm, $[\theta]$ = + 1100°; (+)-p-chlorophenylglycine, less bound, ~215 nm, $[\theta]$ = +240°, thus S configuration and (−)-p-chlorophenylglycine, more bound, ~215 nm, $[\theta]$ = −240°, thus R configuration; (+)-p-carbomethoxyphenylglycine, less bound, ~220 nm, $[\theta]$ = +300°, thus S configuration, and (−)-p-carbomethoxyphenylglycine, more bound, ~220 nm, $[\theta]$ = −310°, thus R configuration; (+)-p-fluorophenylalanine, less bound, ~220 nm, $[\theta]$ = +275°, thus R configuration, and (−)-p-fluorophenylalanine, more bound, ~220 nm, $[\theta]$ = −280°, thus S configuration.

These preparative optical resolutions, performed on compounds never before optically resolved, point to one of the uses of these host-bound resins-that of optically resolving new compounds by a rational process. Graphs 4 and 5 provide examples of the chromatographic curves obtained with the amino ester salts on Columns A and C.

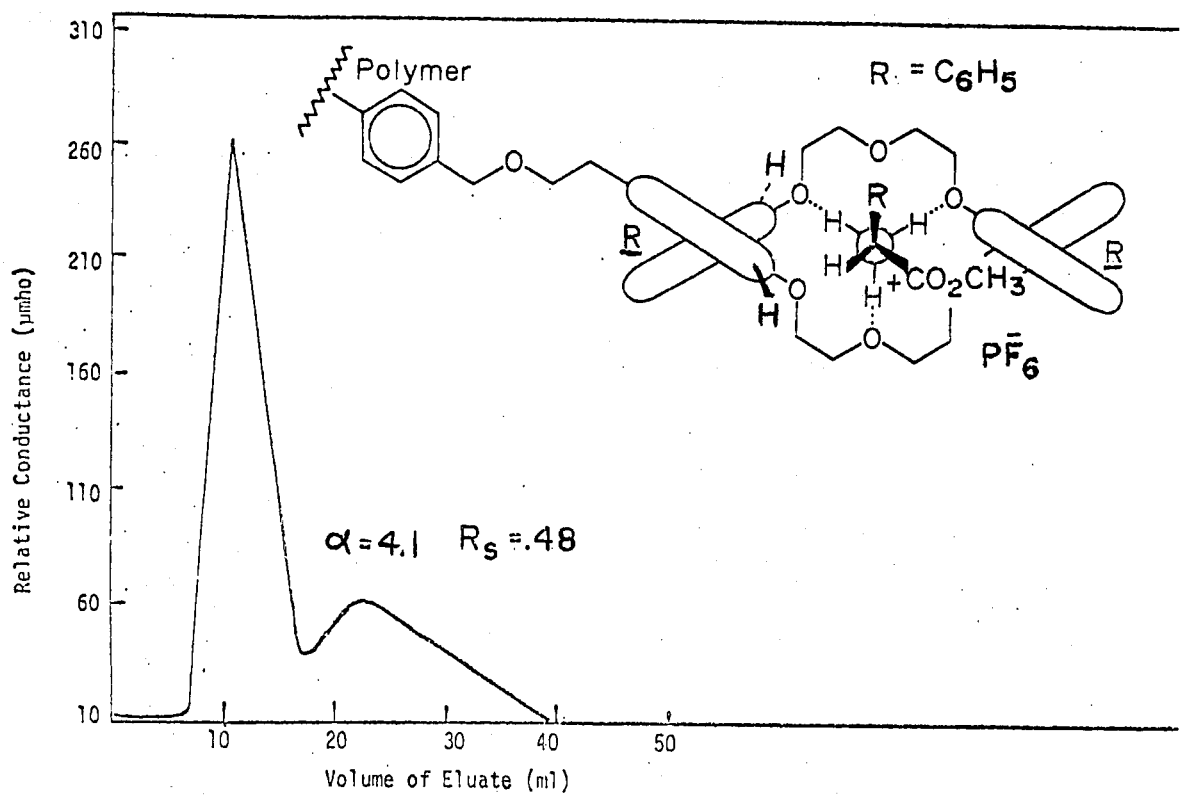

Graph 4 - Plot of Relative Conductance against column Eluate Volume for chromatographic run 1 1 of Table II with (RR)-144 as immobile phase and the methyl ester of phenylglycine hexafluorophosphate in the mobile phase.

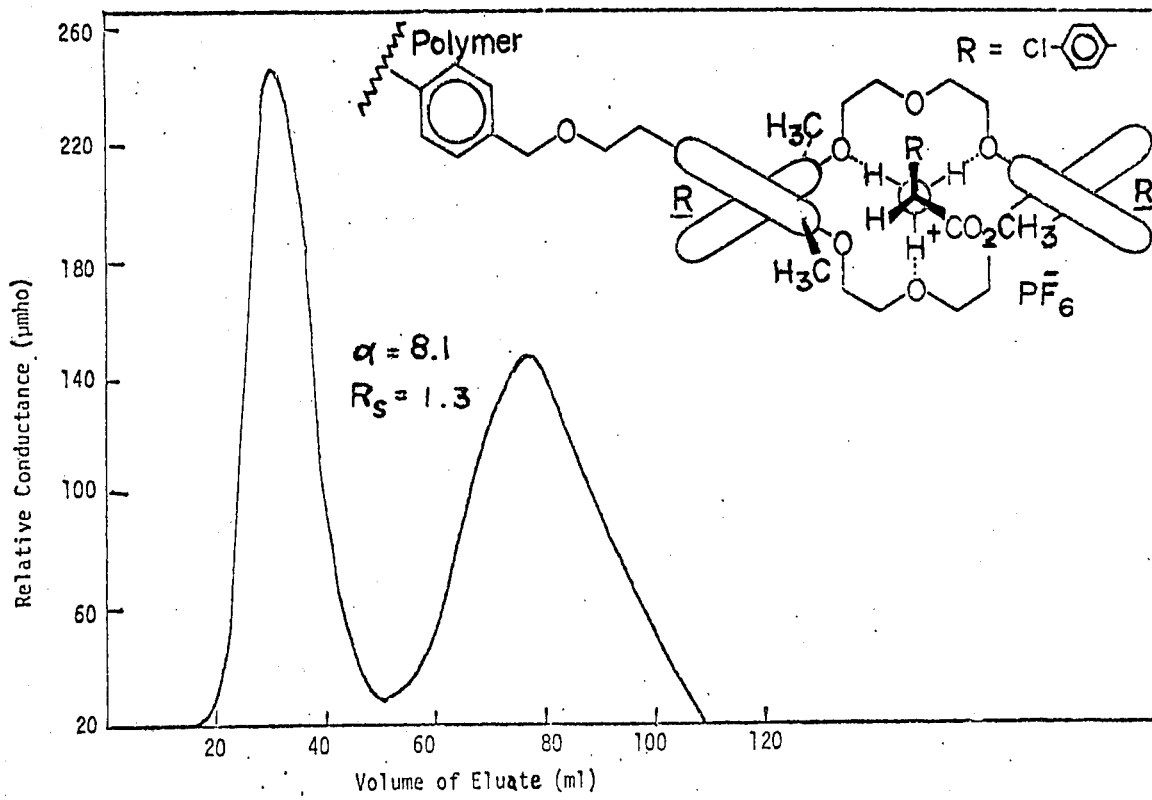

Graph 5 - Plot of Relative Conductance against column Eluate Volume for chromatographic run 12 of Table II with (RR)-145 as immobile phase and the methyl ester of p-chlorophenylglycine hexafluorophosphate in the mobile phase.

Conclusions are as follows. 1) Resin-bound hosts RR-144 and RR-145 provide good chromatographic material for both analytical and preparative resolution of amino ester salts. Three ester salts were resolved for the first time. The best results were obtained when [H]/[G] values were between 36 and 86, and the temperature was zero. 2) Although perchlorate and hexafluorophosphate salts gave similar $\alpha$ values, the perchlorates gave higher $R_s$ values than the hexafluorophosphate salts (compare runs 3 and 4, or 11 and 12). Chloride salts were unsatisfactory. 3) The resin containing the chiral barrier extended by the methyl groups, (RR)-145, gave the higher separation factors ($\alpha$) and the higher efficiencies ($R_x$). 4) Chloroform-acetonitrile mixtures provided the best mobile phases. 5) The configurational relationships involved in the chiral recognition indicate the more stable complex to possess structure 148, except for the ester salts of phenylalanine and p-fluorophenylalanine in which the positions of the R' and $CO_2CH_3$ groups are inverted. The limited data available indicate that the configurations of the more stable complexes and even the extent of chiral recognition follow the same patterns on the resins as in chloroform solutions. In solution the methyl-substituted host exhibited higher chiral recognition than did the nonmethylated, the ester salts of phenylglycine and phenylalanine exhibited opposite chiral preferences, and the ester salt of p-hydroxyphenylglycine exhibited higher chiral recognition than did that of phenylglycine. 6) The inverted preference of (RR)-145 for the (S) enantiomer of phenylalanine as

148

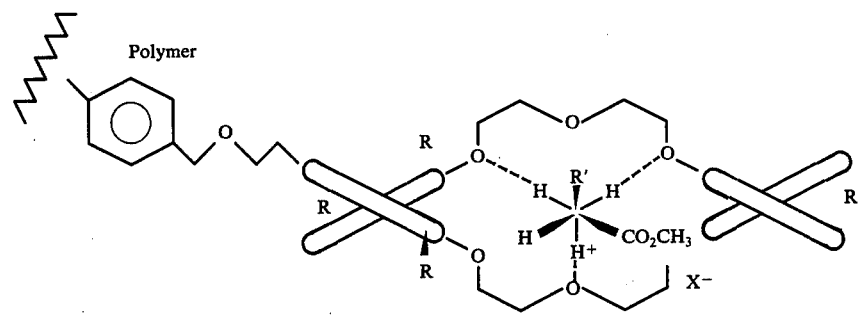

compared to the (R) enantiomer of tyrosine derivatives indicates that substituents in the remote p-positions of the phenyl group seriously affect the direction of chiral recognition (runs 5 and 6, or 14 and 15). Equally striking effects are observed in the phenylglycine ester salt series in which four p-substituents are compared (runs 7-12). In complex 149 (the diastereomer of 148) a naphthalene ring as a potential pi-base is face-to-face with the aryl groups of the guests, whose pi-acid-base characters are determined by their two attached substituents (in the 1,4-positions). The $CHN^+H_3CO_2CH_3$ group is strongly electron withdrawing, and the $CH_2CHN^+H_3CO_2CH_3$ less so. Both make the phenyls weak pi-acids. The p-hydroxyl group decreases relative to p-hydrogen the pi-acidity by electron release, and destabilizes the diastereomer 149. The p-chloro and p-carbomethoxy groups relative to p-hydrogen increase the pi-acidity and stabilize 149. The stability of 148 itself should be free of this effect since aryl pi-pi interactions are absent. Thus values of $\alpha$ depend on the relative stabilities of the less stable diastereomeric complexes (149). A plot of log $\alpha$ against $\rho_p$ for HO, H, $CO_2CH_3$ and Cl (runs 7-12) was nearly linear with $\rho = -0.54$ (correlation coefficient, $-0.84$) [*J. Org. Chem.*, 23, 420 (1958)]. The direction of chiral recognition in the more delicately balanced and less hindered complexes of the phenylalanine series were inverted by changes in the p-substituent, probably due to similar pi-pi interactions [*Bull. Chem. Soc.*, 48, 596 (1975)].

Conclusions

The styrene-divinylbenzene polymer-host compounds of this invention are useful for separating or optically resolving racemic and other mixtures of chemical compounds which contain a primary amino group primarily in a position alpha or beta to a chiral center, e.g., racemic and other mixtures of such amino acids where only one of the optical isomers is useful for preparing dietary and medicinal compounds for animals including humans. These new polymer-host compounds can also be used in analytical procedures for determining optical purity of amines or amino acids, and the like. They can also be used for analyzing what kind and how much of each of the several amino acids is present in a protein hydrolysate. They can be used for determining the absolute configurations of compounds of yet unknown structural configurations.

This invention thus provides a method for resolving chemical enantiomers selected from the group consisting of alkylammonium salts, amino acids and esters and salts of such amino acids, preferably those which contain a primary amino group in a position alpha or beta to a chiral center which comprises passing a liquid solution or mixture containing the mixed enantiomers through a styrene/divinylbenzene resin-bound host compound of formula (III), above, and then recovering the separated enantiomers therefrom, by known procedures. The method of this invention is especially applicable for resolving alpha or beta amino acid compounds, such as the enantiomers of salts of phenylglycine, the d-isomer of which is useful as a reactant forming cephalexin, cephaloglycin and ampicillin antibiotics.

I claim:
1. A compound of the formula

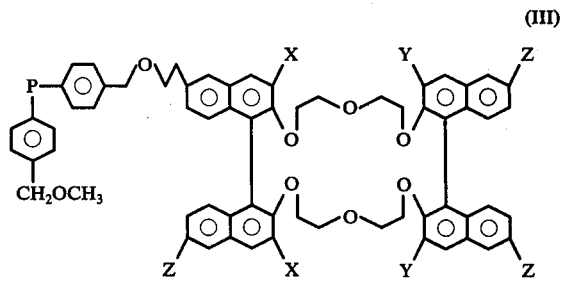

(III)

149

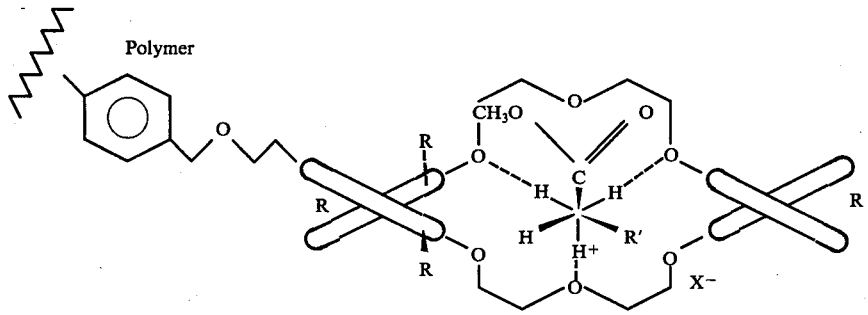

R' = aryl containing groups wherein P is the backbone of a solid styrene-divinylbenzene copolymer, each Z is H or $CH_2CH_2OH$, each X is either H or $CH_3$, each Y is either H or $CH_3$, and the binaphthyl groups of the macrocycle are in the (RR)- or (SS)- configurations.

2. A compound according to claim 1 wherein each X, Y and Z is hydrogen, and the binaphthyl groups of the macrocycle are in the (RR)- or (SS)- configurations.

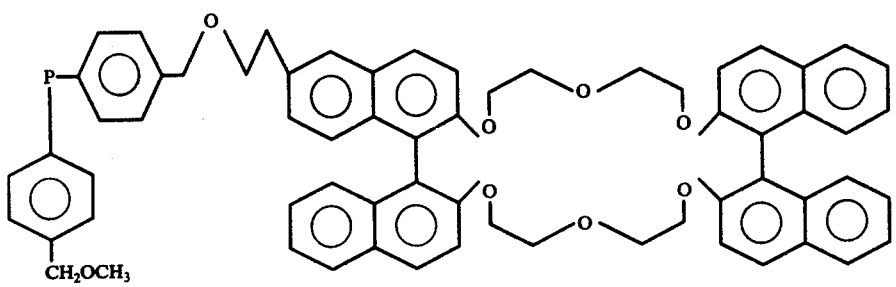

144

3. A compound according to claim 1 wherein each X is methyl, and each Y and Z is hydrogen, and the binaphthyl groups of the macrocycle are in the (RR)- or (SS)-configurations.

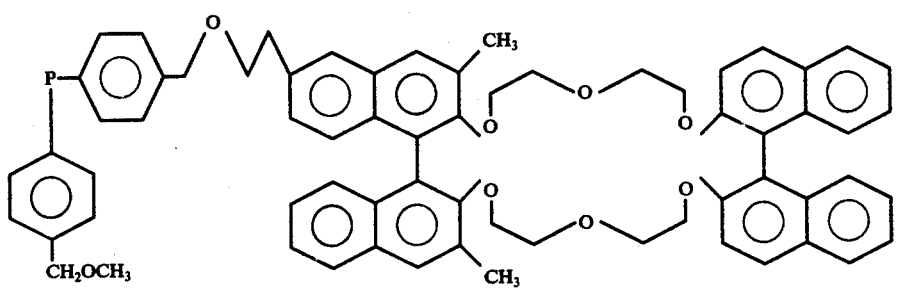

145

4. A compound according to claim 1 wherein each X and each Y is methyl, each Z is hydrogen or CH₂CH₂OH, and the binaphthyl groups of the macrocycle are in the (RR)- or (SS)-configurations.

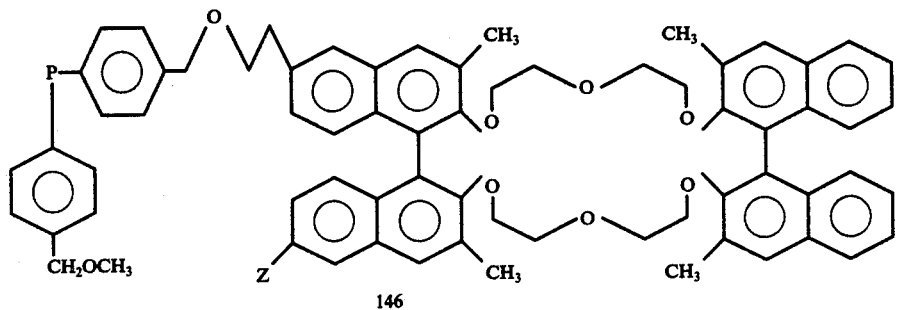

146

5. A compound of the formula

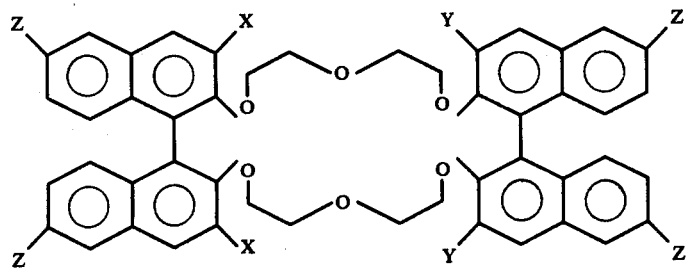

150 wherein at least one Z is —CH₂CH₂OH and the remaining Z moieties are hydrogen or —CH₂CH₂OH, each X is hydrogen or methyl, each Y is hydrogen or methyl, and the binaphthyl groups of the macrocycle are in the (SS) or (RR)-configuration.

6. A compound according to claim 6 wherin one Z is —CH₂CH₂OH and the remaining Z moieties are hydrogen, each X is methyl and each Y is hydrogen.

* * * * *